US009804289B2

(12) United States Patent
Hayler et al.

(10) Patent No.: US 9,804,289 B2
(45) Date of Patent: *Oct. 31, 2017

(54) X-RAY SCANNING SYSTEM AND METHOD

(71) Applicant: United Parcel Service of America, Inc., Atlanta, GA (US)

(72) Inventors: Wendie Patricia Hayler, Atlanta, GA (US); Mark Rutherford, Doncaster (GB); Marcus A. Jones, Roswell, GA (US); Anthony David Kirk, Marietta, GA (US); Gilbert Walter Vanorder, III, Cumming, GA (US); Roy Douglas Hudson, Stoke-on-Trent (GB); Paul Mason, Billingham (GB); James Termini, Doncaster (GB)

(73) Assignee: United Parcel Service of America, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/363,284

(22) Filed: Nov. 29, 2016

(65) Prior Publication Data
US 2017/0075025 A1    Mar. 16, 2017

Related U.S. Application Data

(60) Continuation of application No. 15/244,708, filed on Aug. 23, 2016, now Pat. No. 9,541,667, which is a
(Continued)

(51) Int. Cl.
*G01N 23/00* (2006.01)
*G01V 5/00* (2006.01)
(Continued)

(52) U.S. Cl.
CPC ........... *G01V 5/0016* (2013.01); *G01N 23/04* (2013.01); *G21K 1/10* (2013.01); *G01N 2223/30* (2013.01);
(Continued)

(58) Field of Classification Search
CPC .............................. A61B 6/4291; G21K 1/025
See application file for complete search history.

(56) References Cited

U.S. PATENT DOCUMENTS

| 4,910,759 A | 3/1990 | Sharnoff |
| 6,396,903 B1 | 5/2002 | Wenstrup |

(Continued)

FOREIGN PATENT DOCUMENTS

| CN | 1965373 A | 5/2007 |
| CN | 101326591 A | 12/2008 |

(Continued)

OTHER PUBLICATIONS

International Searching Authority, International Search Report and Written Opinion for International Application No. PCT/US2014/053852, dated Dec. 19, 2014, 12 pages, European Patent Office, The Netherlands.

(Continued)

*Primary Examiner* — Dani Fox
(74) *Attorney, Agent, or Firm* — Alston & Bird LLP

(57) ABSTRACT

Systems and methods are provided for scanning an item utilizing an X-ray scanner in order to facilitate a determination of whether the X-ray radiation penetrated through the entirety of the scanned item. Various embodiments comprise a conveying mechanism, an X-ray emitter, a detector, and an X-ray penetration grid (XPG). The XPG may comprise a radiopaque grid that may serve as a reference for determining whether radiation passes through the scanned item, the grid oriented such that the grid members are neither parallel nor perpendicular to the direction of travel. Such orientation may minimize or eliminate "ghosted" radiation signals included in a visual display of the radiation received by the detector. A scanned item may be oriented with the XPG such that radiation emitted by the X-ray emitter that passes
(Continued)

through a portion of the scanned item must also pass through the XPG before being received by the detector.

20 Claims, 12 Drawing Sheets

Related U.S. Application Data division of application No. 14/475,986, filed on Sep. 3, 2014, now abandoned.

(60) Provisional application No. 61/873,541, filed on Sep. 4, 2013.

(51) Int. Cl.
  *G21K 1/10* (2006.01)
  *G01N 23/04* (2006.01)

(52) U.S. Cl.
  CPC ............ *G01N 2223/3307* (2013.01); *G01N 2223/643* (2013.01)

(56) References Cited

U.S. PATENT DOCUMENTS

| | | | |
|---|---|---|---|
| 7,012,258 B2 | 3/2006 | Groh et al. | |
| 7,277,568 B2 | 10/2007 | Spahn | |
| 7,657,001 B2 | 2/2010 | Van De Haar | |
| 7,831,024 B2 | 11/2010 | Metzler et al. | |
| 7,922,923 B2 | 4/2011 | Tang et al. | |
| 8,243,876 B2 | 8/2012 | Morton | |
| 8,917,812 B2 | 12/2014 | Ikhlef | |
| 9,105,366 B2 | 8/2015 | Hruschka et al. | |
| 9,541,667 B2* | 1/2017 | Hayler | G01N 23/04 |
| 9,686,481 B1 | 6/2017 | Graybill et al. | |
| 2001/0038076 A1 | 11/2001 | Kuwabara | |
| 2002/0037070 A1 | 3/2002 | Tang | |
| 2002/0090055 A1 | 7/2002 | Zur et al. | |
| 2009/0257555 A1 | 10/2009 | Chalmers et al. | |
| 2009/0285353 A1 | 11/2009 | Ellenbogen et al. | |
| 2011/0007871 A1* | 1/2011 | Voorhees | G01N 21/8901 378/57 |
| 2013/0075630 A1* | 3/2013 | Malmin | B23H 1/00 250/505.1 |
| 2013/0188780 A1 | 7/2013 | Hruschka et al. | |
| 2015/0063539 A1 | 3/2015 | Hayler et al. | |
| 2016/0356914 A1 | 12/2016 | Hayler et al. | |

FOREIGN PATENT DOCUMENTS

| | | |
|---|---|---|
| CN | 101379415 A | 3/2009 |
| CN | 103222873 A | 7/2013 |
| DE | 3151436 A1 | 7/1983 |
| DE | 3416716 A1 | 11/1985 |
| EP | 0866378 A2 | 9/1998 |
| EP | 1113290 A2 | 7/2001 |
| EP | 0642264 B1 | 11/2001 |
| EP | 2269513 A1 | 1/2011 |
| EP | 2345589 A1 | 7/2011 |
| JP | H07-063707 A | 3/1995 |
| JP | H10-267867 A | 10/1998 |
| JP | H11-211677 A | 8/1999 |
| JP | 2006-119113 A | 5/2006 |
| JP | 2008-241452 A | 10/2008 |
| JP | 2012-220348 A | 11/2012 |
| WO | WO 2003/100460 A1 | 12/2003 |
| WO | 2007/051092 A2 | 5/2007 |

OTHER PUBLICATIONS

Kabir, Mohammad Zahangir, "Modeling of X-Ray Photoconductors for X-Ray Image Detectors", University of Saskatchewan, Aug. 2005, Retreived from <http://ecommons.usask.ca/handle/10388/etd-08082005-145927> on Oct. 13, 2014, 228 pages.

Starman, Jared, "Lag Correction in Amorphous Silicon Flat-Panel X-Ray Computed Tomography", Stanford University, Dec. 2010, Retrieved from <https://stacks.stanford.edu/file/druid:dj434tf8306/Starman_Jared_thesis_withTitlePage-augmented.pdf> on Oct. 13, 2014, 129 pages.

United States Patent and Trademark Office, Office Action for U.S. Appl. No. 14/475,986, dated Apr. 7, 2015, 11 pages, U.S.A.

United States Patent and Trademark Office, Office Action for U.S. Appl. No. 14/475,986, dated Jul. 27, 2015, 14 pages, U.S.A.

United States Patent and Trademark Office, Office Action for U.S. Appl. No. 14/475,986, dated Jun. 16, 2016, 12 pages, U.S.A.

United States Patent and Trademark Office, Office Action for U.S. Appl. No. 14/475,986, dated Dec. 17, 2015, 11 pages, U.S.A.

United States Patent and Trademark Office, Notice of Allowance for U.S. Appl. No. 15/244,708, dated Nov. 23, 2016, 15 pages, U.S.A.

Canadian Intellectual Property Office, Requisition by the Examiner for Application No. 2,921,990, dated Feb. 6, 2017, 6 pages, Canada.

Japan Patent Office, Notification of Reasons for Refusal for Application No. 2016-540334, dated Feb. 17, 2017, 7 pages, Japan.

Japan Patent Office, Search Report for Application No. 2016-540334, dated Jan. 31, 2017, 41 pages, Japan.

English Translation of CN Office Action dated Jul. 19, 2017 for CN Application No. 201480048720.

CN Office Action dated Jul. 19, 2017 for CN Application No. 201480048720.

* cited by examiner

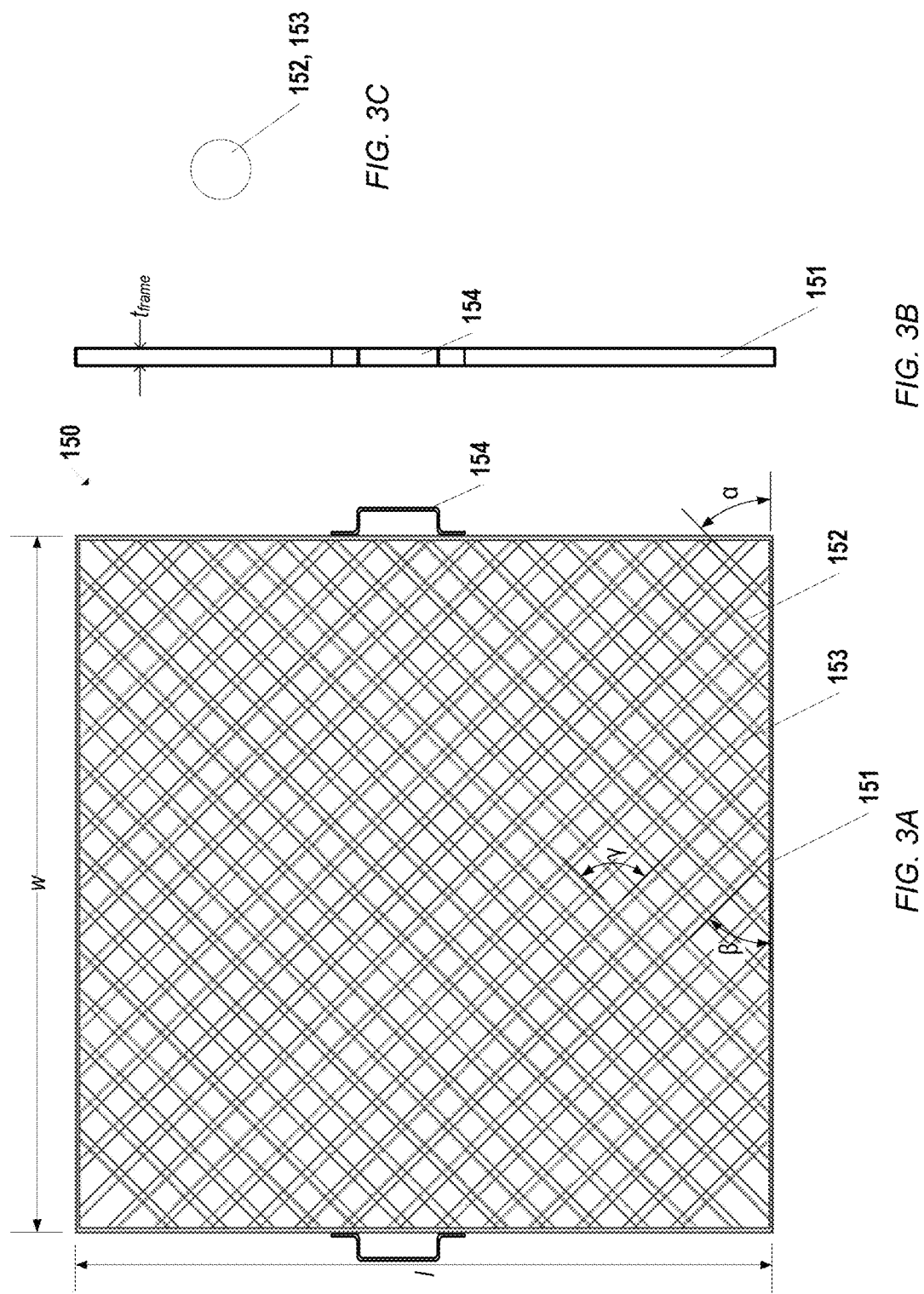

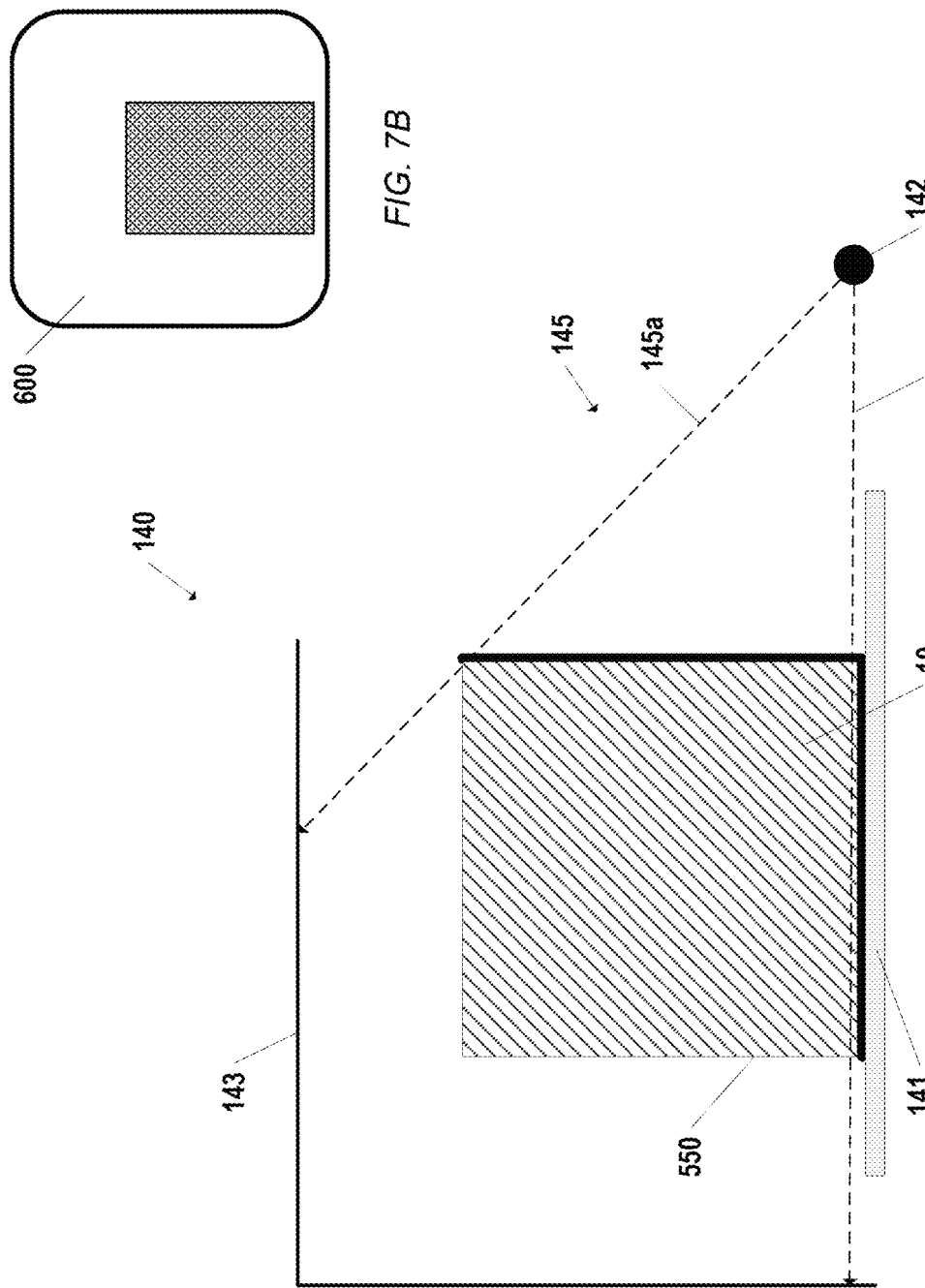

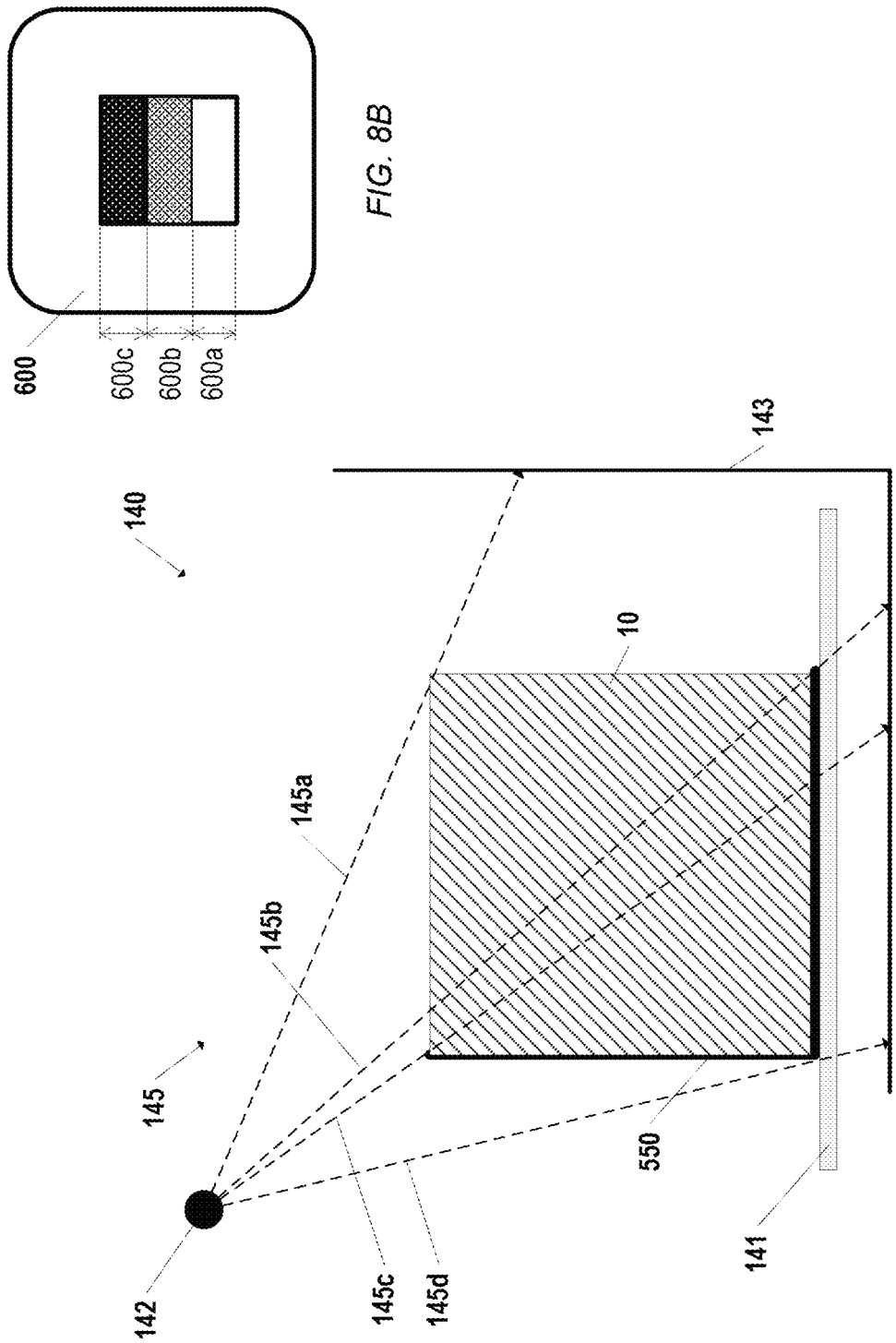

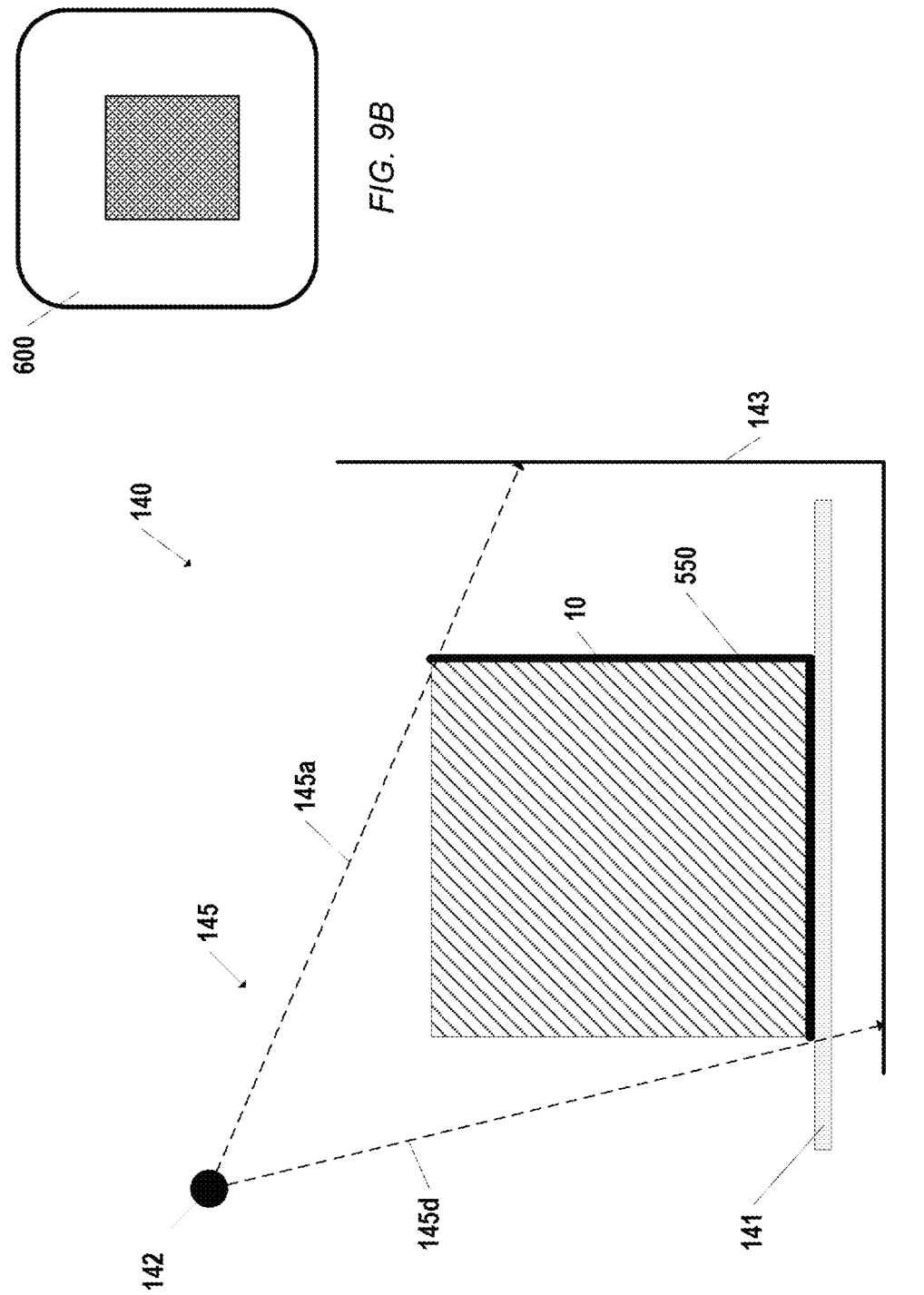

X-RAY SCANNING SYSTEM AND METHOD

CROSS-REFERENCE TO RELATED APPLICATIONS

This patent application is a continuation application filing of U.S. patent application Ser. No. 15/244,708, filed Aug. 23, 2016, which application is a divisional application filing of U.S. patent application Ser. No. 14/475,986, filed Sep. 3, 2014, which application further claims priority to and the benefit of U.S. provisional application Ser. No. 61/873,541, filed Sep. 4, 2013, the contents of all of which as are hereby incorporated herein by reference in their entirety.

BACKGROUND

X-ray scanning devices have historically been used in both the medical and security industries. In security applications, X-ray scanning devices have been used to display the contents of travel bags, shipped items, and/or the like without requiring personnel to undertake the cumbersome task of unpacking and/or disassembling the item in question and subsequently re-packing and/or reassembling the item for further processing. X-ray based security systems have historically been used by airport security entities (e.g., the United States Transportation Security Administration) and common carriers (e.g., United Parcel Service of America, Federal Express, and/or the like) to detect different types of contraband that may be present in items such as baggage, shipping packages, shipping containers, and the like.

In operation, X-ray radiation is transmitted through and/or scattered from items within the baggage, packages, containers, and the like. Various systems incorporate a mesh or grid that is placed upon a conveyor belt along which the baggage, packages, containers, and the like travel during the scanning process. For particularly densely packed baggage, packages, containers, and the like, it is important that X-ray radiation emitted by an X-ray scanning device penetrate the entirety of the scanned item so as to provide a desired degree of certainty that no contraband exists there-within. Conventional mesh or grid structures have proven helpful in this regard by placing such adjacent the baggage, package, container, and the like, opposite a directional orientation of the X-ray scanning device contained within the system. In this manner, such mesh or grid structures provide a baseline indicator of penetration, for example such that if the mesh or grid is visible within a scan, the item has been sufficiently penetrated with the scan for clearance or otherwise.

Although X-ray scanning devices may facilitate the security screening process for items during processing, the physical properties of X-ray radiation and X-ray detectors may, in various circumstances, obscure objects or components visible in an item scan. In general, X-ray radiation may comprise electromagnetic waves having a wavelength between 0.01 and 10 nanometers. Such electromagnetic waves propagate from an X-ray emitter through the item to be scanned, and are collected by a detector positioned opposite the item to be scanned from the X-ray emitter, the detector comprising one or more detector elements configured to measure the intensity of the transmitted radiation (i.e., the electromagnetic wave) along a radiation ray projected from the X-ray emitter to a detector element. In various embodiments, the one or more detector elements may comprise solid-state detectors generally utilized for digital imaging. The solid-state detectors may comprise a luminescent conversion layer, for example, a scintillator (e.g., a cesium iodide scintillator) in which the radiation received by the solid-state detector causes the scintillator to generate light pulses, which may subsequently be converted into digital signals that may be transmitted to a user device and displayed via a display device.

In various circumstances, such conversion layers may maintain or trap radiation, and therefore cause "ghost" images to be created in subsequent intensity signals. Such trapping effects may be caused by, for example, incomplete charge dissipation or low induced energy levels that do not decay prior to receiving additional radiation for a subsequent scan. These residual signals from a previous image remain in the detector and are superimposed on a later generated image. Such effects may become more obvious as the time between successive images is decreased, and the time for previously trapped charge accumulation to decay is likewise decreased. Moreover, stronger electromagnetic signals received by the detector elements may require additional time for the residual electromagnetic signal to decay between images.

As an item to be scanned moves to a scanning location within an X-ray scanning device, the X-ray scanning device may cause ghosted streaks to appear in a generated image. These ghosted streaks may appear as solid lines resembling radiopaque objects present within the scanned item. Where a radiopaque bar or other thin radiopaque object is oriented at least substantially parallel to the direction of travel of the item, ghosted streaks may appear to extend the length of the radiopaque object. Such ghosted streaks may cause an operator viewing the generated image to believe that the X-ray beam penetrated completely through a radiopaque object. Therefore, the operator may erroneously determine that the scanned item is clear of any prohibited items even though a complete scan was not performed on the item.

When associating a mesh or grid structure with items to be scanned, the ghosting phenomenon described above may inadvertently cause at least a portion of the mesh or grid structure to appear visible in the created image, although the electromagnetic waves did not penetrate completely through the item. For example, ghosted streaks may appear to extend at least a portion of the grid elements in the created image and the resulting image may therefore show these ghosted streaks superimposed over items even where the electromagnetic waves did not penetrate completely through the item. Thus, the mesh or grid structure may be "ghosted" (i.e., appear) in a resulting scan image, even where the item being scanned has not, in reality, been fully (or sufficiently) penetrated to actually detect all portions of the conventional mesh or grid. Consequently, personnel viewing the created image may be led to believe that a complete scan through the entirety of an item was achieved. This "ghosting" phenomena is referred to herein as "ghosting," "ghosting lines," "ghost lines," "ghost images," "ghosted images," "ghost radiation," "ghost signals," and/or "ghosted lines," all of which as should be understood to generally and interchangeably describe this phenomena.

Historically, efforts to reduce the impact of ghosting have focused on creating improved detector elements, or incorporating complex algorithms utilized to minimize the impact of ghosting. However, such solutions are prone to errors due at least in part to electromagnetic noise and other imperfections in the received signal. For example, even where grids are used, if such are oriented in a manner that results in the grid lines thereof being parallel to the direction of travel, ghosted lines may appear, although such may contain certain distortions therein. While users could conceivably identify such distortions, the risk of a user overlooking a particular distortion remains prevalent. Thus, a need exists for improved mesh or grid structures that substantially minimize the impact of "ghosting" so as to ensure sufficient penetration of all scanned items without resorting to secondary item handling and the like.

BRIEF SUMMARY

Various embodiments of the present invention are directed to X-ray detector systems for determining the contents of an item. The X-ray detector systems may comprise: (1) an X-ray emitter configured for emitting X-ray radiation; (2) a detector comprising a receiving surface, the detector configured to receive the X-ray radiation and to generate one or more intensity signals indicative of an intensity of the received X-ray radiation at each of a plurality of locations on the receiving surface; (3) an X-ray penetration grid comprising a first grid structure comprising: a perimeter surrounding the X-ray penetration grid having at least a first side, said first side being oriented in a first primary direction; a first plurality of parallel grid members each having a first end and a second end; and a second plurality of parallel grid members each having a first end and a second end; wherein: the first plurality of parallel grid members are coincident with a first plane; the second plurality of parallel grid members are coincident with a second plane; the first plane and the second plane are parallel; the first end and the second end of each of the first plurality of parallel grid members intersects the perimeter at an angle such that the first plurality of parallel grid members are neither parallel nor perpendicular to the first side of the perimeter; and the first end and the second end of each of the second plurality of parallel grid members intersects the perimeter at an angle such that the second plurality of parallel grid members are neither parallel nor perpendicular to the first side of the perimeter; and (4) a conveying mechanism configured for conveying the item and the X-ray penetration grid in a second primary direction to a location between the X-ray emitter and the detector, said second primary direction being substantially the same as the first primary of direction.

Other embodiments of the present invention are direct to computer implemented methods for scanning an item. The computer implemented method comprising steps for: (1) receiving, via a processor, one or more first intensity signals indicative of a first intensity of X-ray radiation received at each of a plurality of locations at a first scan time on a detector, wherein: the detector is configured to receive X-ray radiation from an X-ray emitter and to generate the one or more intensity signals indicative of an intensity of the received X-ray radiation at each of a plurality of locations on the receiving surface; the X-ray radiation is emitted from the X-ray emitter and at least a portion of the X-ray radiation passes through the item and an X-ray penetration grid before being received by the detector, wherein: the X-ray penetration grid comprises a first grid structure comprising: a perimeter surrounding the X-ray penetration grid having at least a first side, said first side being oriented in a first primary direction; a first plurality of parallel grid members each having a first end and a second end; and a second plurality of parallel grid members each having a first end and a second end; wherein: the first plurality of parallel grid members are coincident with a first plane; the second plurality of parallel grid members are coincident with a second plane; the first plane and the second plane are at least substantially parallel; the first end and the second end of each of the first plurality of parallel grid members intersects the perimeter at an angle such that the first plurality of parallel grid members are neither parallel nor perpendicular to the first side of the perimeter; and the first end and the second end of each of the second plurality of parallel grid members intersects the perimeter at an angle such that the second plurality of parallel grid members are neither parallel nor perpendicular to the first side of the perimeter; and the item and the X-ray penetration grid are propelled in a second primary direction, said second primary direction being substantially the same as the first primary direction; (2) causing, via a display device, display of the one or more first intensity signals; (3) receiving, via the processor, one or more second intensity signals indicative of one or more ghosted image extending from an edge of the item; (4) causing, via the display device, display of the one or more second intensity signals, wherein the displayed second intensity signals comprises a radiation ghost based at least in part on the one or more ghosted image; and (5) identifying, via the one or more processors, the presence of a radiation ghost based at least in part on the second intensity signals.

Alternative embodiments of the present invention are directed to X-ray penetration grids comprising a first grid structure comprising: (1) a perimeter surrounding the grid structure having at least a first side; (2) a first plurality of parallel grid members each having a first end and a second end; and (3) a second plurality of parallel grid members each having a first end and a second end; wherein: the first plurality of parallel grid members are coincident with a first plane; the second plurality of parallel grid members are coincident with a second plane; the first plane and the second plane are parallel; the first end and the second end of each of the first plurality of parallel grid members intersects the perimeter at an angle such that the first plurality of parallel grid members are neither parallel nor perpendicular to the first side of the perimeter; and the first end and the second end of each of the second plurality of parallel grid members intersects the perimeter at an angle such that the second plurality of parallel grid members are neither parallel nor perpendicular to the first side of the perimeter. In various embodiments, the X-ray penetration grid may additionally comprise a second grid structure comprising: (1) a second perimeter surrounding the second grid structure having at least a first side; (2) a third plurality of parallel grid members each having a first end and a second end; and (3) a fourth plurality of parallel grid members each having a first end and a second end; wherein the third plurality of parallel grid members are coincident with a third plane; the fourth plurality of parallel grid members are coincident with a fourth plane; the third plane and the fourth plane are parallel; the first end and the second end of each of the third plurality of parallel grid members intersects the second perimeter at an angle such that the third plurality of parallel grid members are neither parallel nor perpendicular to the first side of the second perimeter; the first end and the second end of each of the fourth plurality of parallel grid members intersects the perimeter at an angle such that the fourth plurality of parallel grid members are neither parallel nor perpendicular to the first side of the second perimeter; and the third plane and the fourth plane are perpendicular to the first plane and the second plane.

BRIEF DESCRIPTION OF THE SEVERAL VIEWS OF THE DRAWINGS

Reference will now be made to the accompanying drawings, which are not necessarily drawn to scale, and wherein:

FIGS. 3A-3C illustrate an X-ray Penetration Grid according to various embodiments;

FIGS. 7A-7B are schematic diagrams of an X-ray Penetration Grid used with an X-ray scanner and a corresponding visual display according to various embodiments;

FIGS. 8A-8B are schematic diagrams of an X-ray Penetration Grid used with an X-ray scanner and a corresponding visual display according to various embodiments;

FIGS. 9A-9B are schematic diagrams of an X-ray Penetration Grid used with an X-ray scanner and a corresponding visual display according to various embodiments;

DETAILED DESCRIPTION

Figure 1:
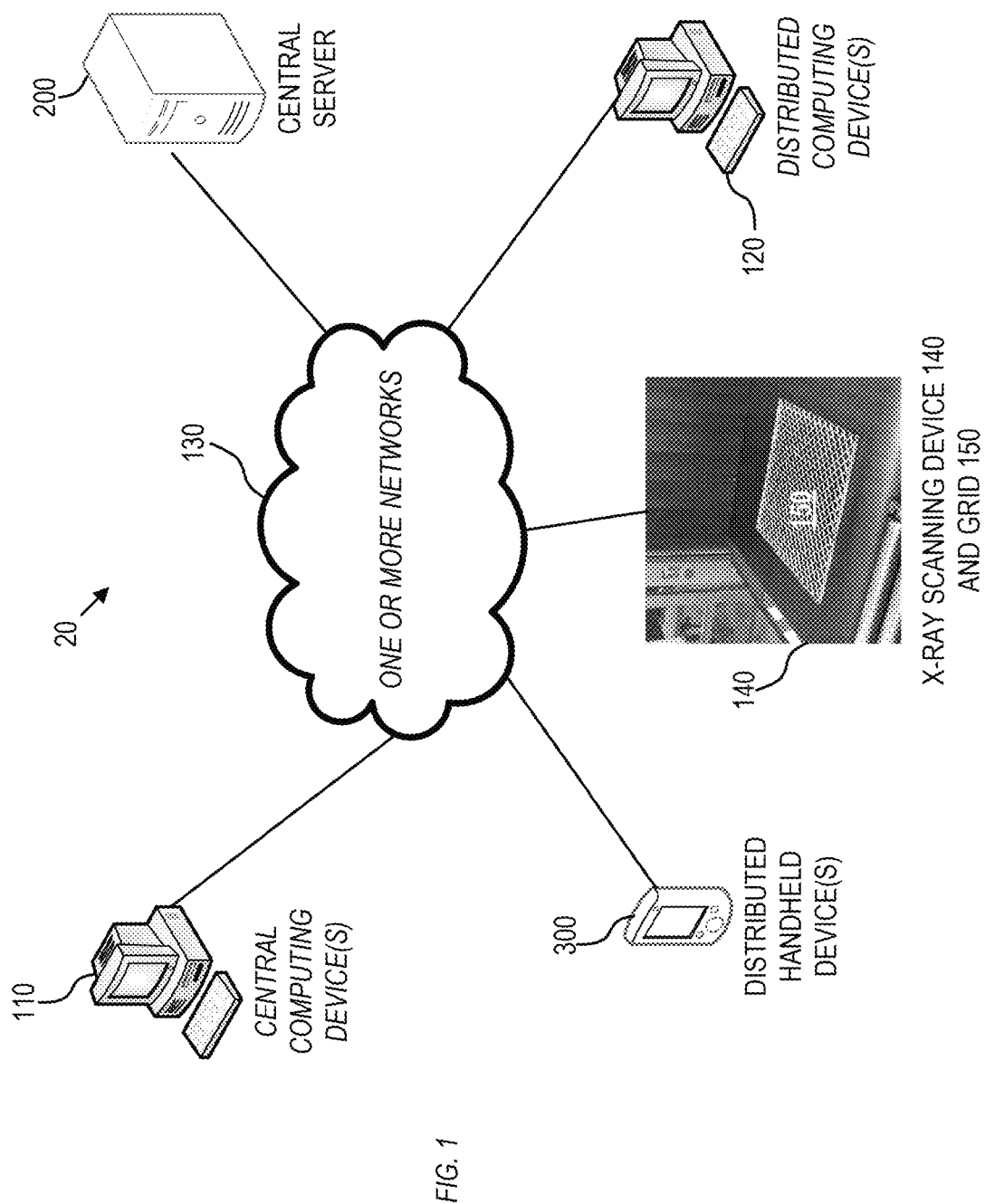
FIG. 1 shows a block diagram of a system according to various embodiments.

The present invention will now be described more fully hereinafter with reference to the accompanying drawings, in which some, but not all embodiments of the invention are shown. Indeed, the invention may be embodied in many different forms and should not be construed as limited to the embodiments set forth herein. Rather, these embodiments are provided so that this disclosure will satisfy applicable legal requirements. Like numbers refer to like elements throughout.

Overview

Various embodiments are directed to a system for identifying radiopaque objects present in an item scanned using an X-ray scanning device. The system may comprise an X-ray scanning device comprising an X-ray emitter and a detector, a conveying mechanism, and an X-ray penetration grid. The X-ray penetration grid may comprise a radiopaque grid oriented such that the radiopaque grid elements are neither parallel nor perpendicular to the direction of travel of the conveying mechanism. In use, the item to be scanned is oriented relative to the X-ray penetration grid such that, when the item and X-ray penetration grid are located between the X-ray emitter and the detector, X-ray waves produced by the X-ray emitter that pass through the item to be scanned must also pass through the X-ray penetration grid before reaching the detector. Because the radiopaque grid elements are evenly spaced apart and neither parallel nor perpendicular to the direction of travel of the conveying mechanism, no ghosted grid elements are visible in the generated image, such that radiopaque objects contained in a scanned item are easily and/or accurately identified in the generated image.

Moreover, various embodiments are directed to methods for identifying radiopaque objects present in an item scanned using an X-ray scanning device. An item is placed on a conveying mechanism with an X-ray penetration grid, and is propelled into an X-ray scanner device. As the item and X-ray penetration grid is scanned, a detector receives radiation emitted from an X-ray emitter that corresponds to the relative intensity of the radiation penetrating the item and X-ray penetration grid and generates intensity signals indicative of the relative intensity of the radiation received at various locations on the detector. The detector then converts the signals indicative of the relative intensity of the received radiation into visible signals, which may be transmitted via a network to one or more computing devices. In certain embodiments the X-Ray scanning device may be configured to scan multiple slices of each scanned item corresponding to different locations along the length of the scanned item (the length of the scanned item being parallel to the direction of travel). The one or more computing devices subsequently display the visible signals to a user monitoring the X-ray scanning device by piecing together the individual slices of the item. At least in part because the radiopaque grid elements are spaced evenly and are neither parallel nor perpendicular to the direction of travel of the conveying mechanism, the ghost lines are substantially, and in certain embodiments entirely, eliminated such that virtually no ghost lines are visible in the displayed visual image.

Exemplary Apparatuses, Methods, Systems, Computer Program Products, & Computing Entities Embodiments of the present invention may be implemented in various ways, including as computer program products. A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM)), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (Fe-RAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAIVI), Thyristor RAM (T-RAM), Zero-capacitor (Z-RAM), Rambus in-line memory module (RIMM), dual in-line memory module (DIMM), single in-line memory module (SIMM), video random access memory VRAM, cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. However, embodiments of the present invention may also take the form of an entirely hardware embodiment performing certain steps or operations.

Various embodiments are described below with reference to block diagrams and flowchart illustrations of apparatuses, methods, systems, and computer program products. It should be understood that each block of any of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions and program instructions for performing the specified functions. It should also be understood that each block of the block diagrams and flowchart illustrations, and combinations of blocks in the block diagrams and flowchart illustrations, could be implemented by special purpose hardware-based computer systems that perform the specified functions or operations, or combinations of special purpose hardware and computer instructions.

Exemplary Architecture of System 20

FIG. 1 is a block diagram of an X-ray penetration system 20 that can be used in conjunction with various embodiments of the present invention. In at least the illustrated embodiment, the system 20 may include one or more central computing devices 110, one or more distributed computing devices 120, one or more distributed handheld or mobile devices 300, and at least one conveying mechanism 140 and X-ray penetration grid 150, all configured in communication with a central server 200 via one or more networks 130. While FIG. 1 illustrates the various system entities as separate, standalone entities, the various embodiments are not limited to this particular architecture.

According to various embodiments of the present invention, the one or more networks 130 may be capable of supporting communication in accordance with any of a number of second-generation (2G), 2.5G, third-generation (3G), and/or fourth-generation (4G) mobile communication protocols, or the like. More particularly, the one or more networks 130 may be capable of supporting communication in accordance with 2G wireless communication protocols IS-136 (TDMA), GSM, and IS-95 (CDMA). Also, for example, the one or more networks 130 may be capable of supporting communication in accordance with 2.5G wireless communication protocols GPRS, Enhanced Data GSM Environment (EDGE), or the like. In addition, for example, the one or more networks 130 may be capable of supporting communication in accordance with 3G wireless communication protocols such as Universal Mobile Telephone System (UMTS) network employing Wideband Code Division Multiple Access (WCDMA) radio access technology. Some narrow-band AMPS (NAMPS), as well as TACS, network(s) may also benefit from embodiments of the present invention, as should dual or higher mode mobile stations (e.g., digital/analog or TDMA/CDMA/analog phones). As yet another example, each of the components of the system 5 may be configured to communicate with one another in accordance with techniques such as, for example, radio frequency (RF), Bluetooth™ infrared (IrDA), or any of a number of different wired or wireless networking techniques, including a wired or wireless Personal Area Network ("PAN"), Local Area Network ("LAN"), Metropolitan Area Network ("MAN"), Wide Area Network ("WAN"), or the like.

Although the device(s) 110-300 are illustrated in FIG. 1 as communicating with one another over the same network 130, these devices may likewise communicate over multiple, separate networks.

According to one embodiment, in addition to receiving data from the server 200, the distributed devices 110, 120, 140, and/or 300 may be further configured to collect and transmit data on their own. In various embodiments, the devices 110, 120, 140, and/or 300 may be capable of receiving data via one or more input units or devices, such as a keypad, touchpad, barcode scanner, radio frequency identification (RFID) reader, interface card (e.g., modem, etc.) or receiver. The devices 110, 120, 140, and/or 300 may further be capable of storing data to one or more volatile or non-volatile memory modules, and outputting the data via one or more output units or devices, for example, by displaying data to the user operating the device, or by transmitting data, for example over the one or more networks 130.

Exemplary Server 200

In various embodiments, the server 200 includes various systems for performing one or more functions in accordance with various embodiments of the present invention, including those more particularly shown and described herein. It should be understood, however, that the server 200 might include a variety of alternative devices for performing one or more like functions, without departing from the spirit and scope of the present invention. For example, at least a portion of the server 200, in certain embodiments, may be located on the distributed device(s) 110, 120, 140 and/or the handheld or mobile device(s) 300, as may be desirable for particular applications. As will be described in further detail below, in at least one embodiment, the handheld or mobile device(s) 300 may contain one or more mobile applications 330 which may be configured so as to provide a user interface for communication with the server 200, all as will be likewise described in further detail below.

Figure 2A:
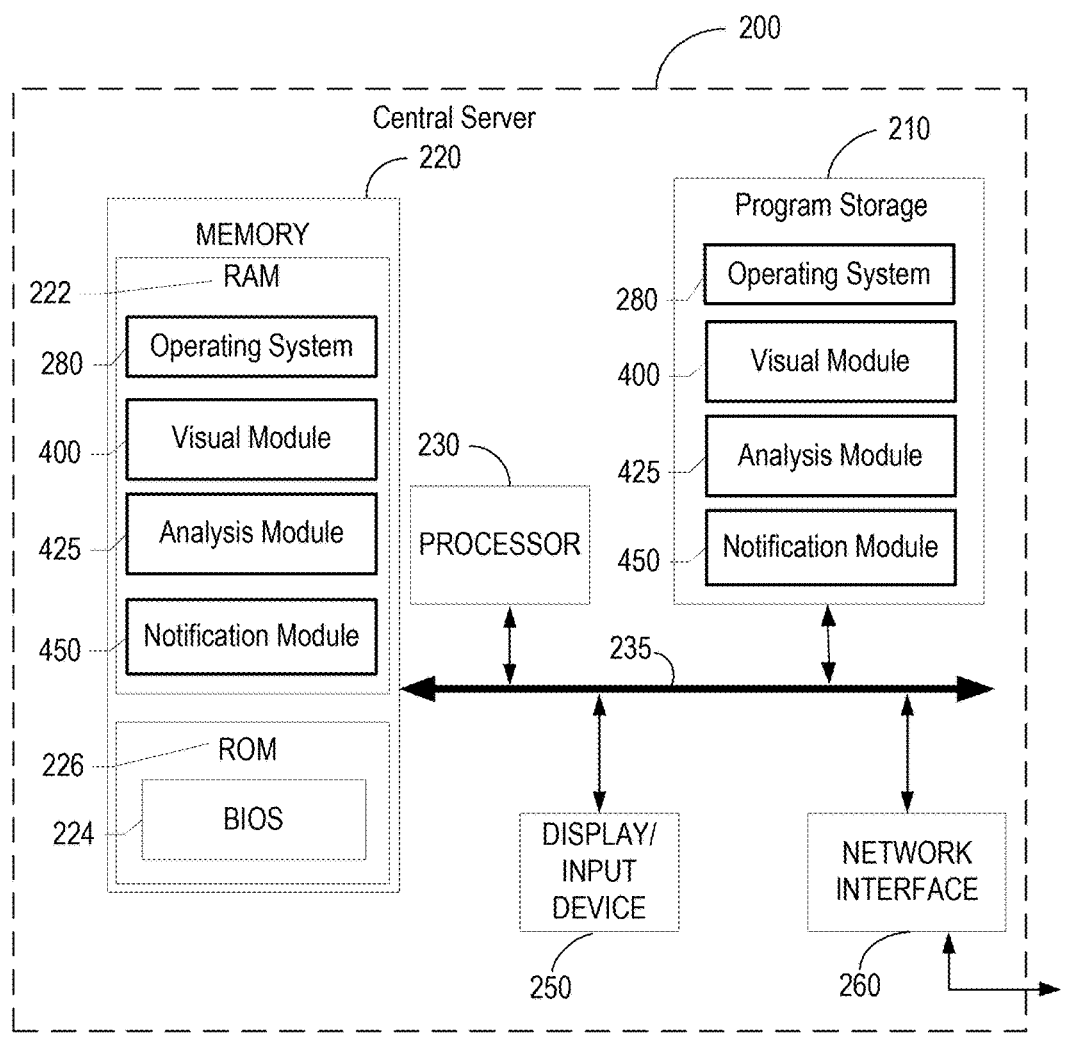
FIG. 2A is a schematic block diagram of a server according to various embodiments.

FIG. 2A is a schematic diagram of the server 200 according to various embodiments. The server 200 includes a processor 230 that communicates with other elements within the server via a system interface or bus 235. Also included in the server 200 is a display/input device 250 for receiving and displaying data. This display/input device 250 may be, for example, a keyboard or pointing device that is used in combination with a monitor. The server 200 further includes memory 220, which preferably includes both read only memory (ROM) 226 and random access memory (RAM) 222. The server's ROM 226 is used to store a basic input/output system 224 (BIOS), containing the basic routines that help to transfer information between elements within the server 200. Various ROM and RAM configurations have been previously described herein.

In addition, the server 200 includes at least one storage device or program storage 210, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 210 are connected to the system bus 235 by an appropriate interface. The storage devices 210 and their associated computer-readable media provide nonvolatile storage for a personal computer. As will be appreciated by one of ordinary skill in the art, the computer-readable media described above could be replaced by any other type of computer-readable media known in the art. Such media include, for example, magnetic cassettes, flash memory cards, digital video disks, and Bernoulli cartridges.

Although not shown, according to an embodiment, the storage device 210 and/or memory of the server 200 may further provide the functions of a data storage device, which may store historical and/or current delivery data and delivery conditions that may be accessed by the server 200. In this regard, the storage device 210 may comprise one or more databases. The term "database" refers to a structured collection of records or data that is stored in a computer system, such as via a relational database, hierarchical database, or network database and as such, should not be construed in a limiting fashion.

A number of program modules 400, 425, 450 comprising, for example, one or more computer-readable program code portions executable by the processor 230, may be stored by the various storage devices 210 and within RAM 222. Such program modules may also include an operating system 280. In these and other embodiments, the various modules 400, 425, 450 control certain aspects of the operation of the server 200 with the assistance of the processor 230 and operating system 280. For example, a Visual Module 400 may be configured to covert signals received from the X-ray scanning device 140 into visible signals to be displayed via the display/input device 250; an Analysis Module 425 may be configured to identify a visual ghosting phenomenon; and a Notification Module 450 may be configured to notify relevant personnel of the presence of a ghosting phenomenon in a presented visual display. In still other embodiments, it should be understood that one or more additional and/or alternative modules may also be provided, without departing from the scope and nature of the present invention.

In various embodiments, the program modules 400, 425, 450 are executed by the server 200 and are configured to generate one or more graphical user interfaces, reports, instructions, and/or notifications/alerts, all accessible and/or transmittable to various users of the system 20. In certain embodiments, the user interfaces, reports, instructions, and/or notifications/alerts may be accessible via one or more networks 130, which may include the Internet or other feasible communications network, as previously discussed.

In various embodiments, it should also be understood that one or more of the modules 400, 425, 450 may be alternatively and/or additionally (e.g., in duplicate) stored locally on one or more of the devices 110, 120, 140, and/or 300 and may be executed by one or more processors of the same. According to various embodiments, the modules 400, 425, 450 may send data to, receive data from, and utilize data contained in one or more databases, which may be comprised of one or more separate, linked and/or networked databases.

Also located within the server 200 is a network interface 260 for interfacing and communicating with other elements of the one or more networks 130. It will be appreciated by one of ordinary skill in the art that one or more of the server 200 components may be located geographically remotely from other server components. Furthermore, one or more of the server 200 components may be combined, and/or additional components performing functions described herein may also be included in the server.

While the foregoing describes a single processor 230, as one of ordinary skill in the art will recognize, the server 200 may comprise multiple processors operating in conjunction with one another to perform the functionality described herein. In addition to the memory 220, the processor 230 can also be connected to at least one interface or other means for displaying, transmitting and/or receiving data, content or the like. In this regard, the interface(s) can include at least one communication interface or other means for transmitting and/or receiving data, content or the like, as well as at least one user interface that can include a display and/or a user input interface, as will be described in further detail below. The user input interface, in turn, can comprise any of a number of devices allowing the entity to receive data from a user, such as a keypad, a touch display, a joystick or other input device.

Still further, while reference is made to the "server" 200, as one of ordinary skill in the art will recognize, embodiments of the present invention are not limited to traditionally defined server architectures. Still further, the system of embodiments of the present invention is not limited to a single server, or similar network entity or mainframe computer system. Other similar architectures including one or more network entities operating in conjunction with one another to provide the functionality described herein may likewise be used without departing from the spirit and scope of embodiments of the present invention. For example, a mesh network of two or more personal computers (PCs), similar electronic devices, or handheld portable devices, collaborating with one another to provide the functionality described herein in association with the server 200 may likewise be used without departing from the spirit and scope of embodiments of the present invention.

According to various embodiments, many individual steps of a process may or may not be carried out utilizing the computer systems and/or servers described herein, and the degree of computer implementation may vary, as may be desirable and/or beneficial for one or more particular applications.

Distributed Handheld (or Mobile) Device(s) 300

Figure 2B:
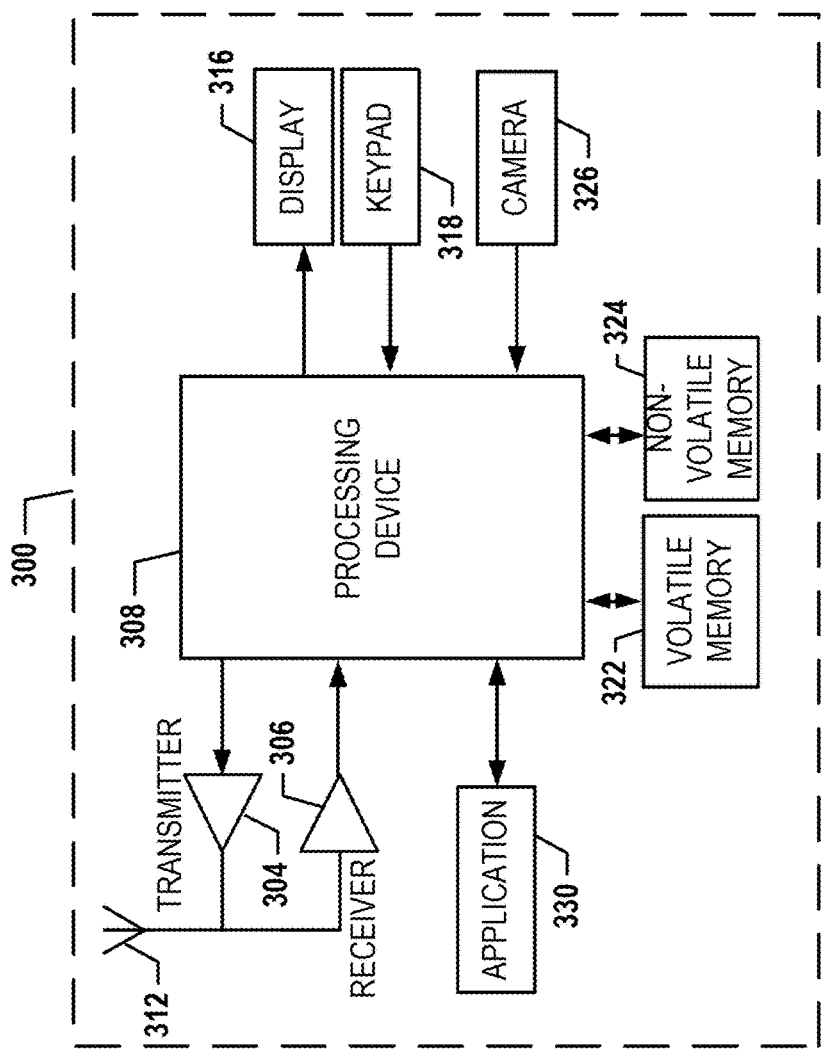
FIG. 2B is a schematic block diagram of an exemplary mobile device according to various embodiments.

FIG. 2B provides an illustrative schematic representative of a mobile device 300 that can be used in conjunction with various embodiments of the present invention. Mobile devices 300 can be operated by various parties. As shown in FIG. 2B, a mobile device 300 may include an antenna 312, a transmitter 304 (e.g., radio), a receiver 306 (e.g., radio), and a processing element 308 that provides signals to and receives signals from the transmitter 304 and receiver 306, respectively.

The signals provided to and received from the transmitter 304 and the receiver 306, respectively, may include signaling data in accordance with an air interface standard of applicable wireless systems to communicate with various entities, such as the server 200, the distributed devices 110, 120, 140 and/or the like. In this regard, the mobile device 300 may be capable of operating with one or more air interface standards, communication protocols, modulation types, and access types. More particularly, the mobile device 300 may operate in accordance with any of a number of wireless communication standards and protocols. In a particular embodiment, the mobile device 300 may operate in accordance with multiple wireless communication standards and protocols, such as GPRS, UMTS, CDMA2000, 1xRTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the mobile device 300 may according to various embodiments communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The mobile device 300 can also download changes, add-ons, and updates, for instance, to its firmware, software (e.g., including executable instructions, applications, program modules), and operating system.

According to one embodiment, the mobile device 300 may include a location determining device and/or functionality. For example, the mobile device 300 may include a GPS module adapted to acquire, for example, latitude, longitude, altitude, geocode, course, and/or speed data. In one embodiment, the GPS module acquires data, sometimes known as ephemeris data, by identifying the number of satellites in view and the relative positions of those satellites.

The mobile device 300 may also comprise a user interface (that can include a display 316 coupled to a processing element 308) and/or a user input interface (coupled to a processing element 308). The user input interface can comprise any of a number of devices allowing the mobile device 300 to receive data, such as a keypad 318 (hard or soft), a touch display, voice or motion interfaces, or other input device. In embodiments including a keypad 318, the keypad can include (or cause display of) the conventional numeric (0-9) and related keys (#, *), and other keys used for operating the mobile device 300 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The mobile device 300 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database mapping systems, data, applications, programs, program modules, scripts, source code, object code, byte code, compiled code, interpreted code, machine code, executable instructions, and/or the like to implement the functions of the mobile device 300.

The mobile device 300 may also include one or more of a camera 326 and a mobile application 330. The camera 326 may be configured according to various embodiments as an additional and/or alternative data collection feature, whereby one or more items may be read, stored, and/or transmitted by the mobile device 300 via the camera. The mobile application 330 may further provide a feature via which various tasks may be performed with the mobile device 300. Various configurations may be provided, as may be desirable for one or more users of the mobile device 300 and the system 20 as a whole.

X-Ray Penetration Grid (XPG)

FIGS. 3A-3C illustrate an exemplary XPG 150 according to various embodiments. As shown therein, an XPG 150 may comprise a frame 151, a first plurality of grid members 152, and a second plurality of grid members 152. In various embodiments, one or more handles 154 may be coupled to the frame 151 to facilitate transportation of the XPG 150. In various embodiments, an XPG 150 may comprise 4 or more handles 154. Such handles 154 may be located at least substantially near the center point of each side of the XPG 150. Alternatively, such handles may be located at least substantially near each corner of the XPG 150. Any of a variety of configurations and handle locations as maybe desirable are possible.

FIG. 3A illustrates a top view of an XPG 150 according to various embodiments. As shown therein, the frame 151 may be at least substantially rectangular, and may be at least substantially square in shape, although substantially any shape may be utilized. As a non-limiting example, the sides of the XPG 150 need not be parallel or perpendicular, and may have a parallelogram shape. In various embodiments, the XPG 150 may be sized such that the XPG fits onto a conveying mechanism 141, onto a pallet, onto a trailer, or onto other vehicles that may travel through an X-ray scanning device 140 with an item 10 to be scanned. As non-limiting examples, the sides of the XPG 150 may be at least substantially 800 mm in length, or at least substantially 516 mm in length.

In various embodiments, the first plurality of grid members 152 and second plurality of grid members 153 may each comprise a plurality of at least substantially parallel grid members spaced at substantially equivalent intervals (e.g., 1 inch). Alternatively, the first plurality of grid members 152 may comprise a plurality of at least substantially parallel grid members spaced at varying intervals. Likewise, the second plurality of grid members 153 may comprise a plurality of at least substantially parallel grid members spaced at varying intervals. Moreover, the first plurality of grid members 152 may be spaced at intervals different from the spacing intervals of the second plurality of grid members 153, such that the resulting spaces between the grid members have varying side lengths. As a non-limiting example, the spaces between the grid members 152, 153 may be rectangular in shape and have multiple side lengths.

The first plurality of grid members 152 may reside within a first plane that is parallel to, and spaced apart from, a second plane in which the second plurality of grid members 153 resides. Alternatively, the first plane and second plane may be coincident, such that the first plurality of grid members 152 and second plurality of grid members 153 reside in a single plane.

In various embodiments, the grid members 152, 153 may be elongated rods having a circular cross-section (as described herein), although any of a variety of cross-sectional shapes may be utilized (e.g., square, rectangular, triangular, circular, and/or the like). The first plurality of grid members 152 and second plurality of grid members 153 may be coupled to the frame 151 of the XPG 150 using one or more fasteners. As a non-limiting example, such fasteners may comprise a weld, an ultrasonic weld, an adhesive, a screw, a bolt, and/or the like. Similarly, one or more of the first plurality of grid members 152 may be coupled to one or more of the second plurality of grid members 153 using one or more fasteners such as those described above. In various embodiments, one or more of the first plurality of grid members 152 may be coupled (e.g., welded) to one or more of the second plurality of grid members 153 at one or more cross points defined as each location within the XPG 150 where one of the first plurality of grid members 152 is in contact with one of the second plurality of grid members 153. As a non-limiting example, the first plurality of grid members 152 is coupled (e.g., welded) to the second plurality of grid members 153 at each cross point.

As illustrated in FIG. 3A, the first plurality of grid members 152 crosses the second plurality of grid members 153 at an angle γ. In various embodiments, the angle γ is between 75 degrees and 105 degrees, although preferably at least substantially 90 degrees. In various embodiments, the first plurality of grid members 152 and second plurality of grid members 153 may have at least substantially equivalent spacing, such that the resulting gaps within the grid or mesh structure are at least substantially square (e.g., 1 inch squares). Moreover, the first plurality of grid members 152 and second plurality of grid members 153 intersect the frame 151 at angles α and β, respectively. In various embodiments, angles α and β are between 30 degrees and 55 degrees, although preferably at least substantially 45 degrees. In various embodiments where angle γ is 90 degrees, angles α and β may be equivalent. As illustrated in FIG. 3A, the XPG 150 may have a length l and a width w. In various embodiments the length l and width w may be at least substantially equivalent, such that the XPG 150 is square in shape. As non-limiting examples, the length l and width w may be 800 mm or 516 mm. However, the length l and width w need not be equivalent.

FIG. 3B illustrates a side view of an XPG 150 according to various embodiments. As illustrated in FIG. 3B, the frame 151 may have a thickness $t_{frame}$ sized such that $t_{frame}$ is at least as large as the combined diameter, width, thickness, height, or other words used herein, of the first plurality of grid members 152 and second plurality of grid members 153. In various embodiments, the first plurality of grid members 152 and second plurality of grid members 153 may be in separate parallel planes, such that the first plurality of grid members 152 may be substantially adjacent the second plurality of grid members 153 such that the first plurality of grid members is above the second plurality of grid members when the XPG 150 is placed horizontally. Alternatively, the first plurality of grid members 152 and second plurality of grid members 153 may be in coincident planes, such that segments of each of the second plurality of grid members resides between each of the first plurality of grid members, or vice versa. As a non-limiting example, the second plurality of grid members 153 may be discontinuous elements, such that segments of each of the second plurality of grid members resides between continuous grid members of the first plurality of grid members 152. Where the first plurality of grid members 152 and second plurality of grid members 153 reside in different planes, each of the plurality of grid members 152, 153 may be continuous elements.

FIG. 3C illustrates an exemplary cross sectional view of a grid member such as that in the first plurality of grid members 152 and second plurality of grid members 153. As shown therein, the grid members 152, 153 may have an at least substantially circular cross section, although any of a variety of cross-sectional shapes may be utilized (e.g., square, rectangular, triangular, circular, and/or the like).

Moreover, the first plurality of grid members 152 and second plurality of grid members 153 may be radiopaque, such that radiation does not pass through the grid members. As a non-limiting example, the grid members 152, 153 may comprise 6 mm diameter solid steel bars configured to prevent X-ray radiation from passing through the grid members. Alternatively, any of a variety of radiopaque materials (e.g., lead) and configurations (e.g., hollow bars) may be utilized.

Figure 4:
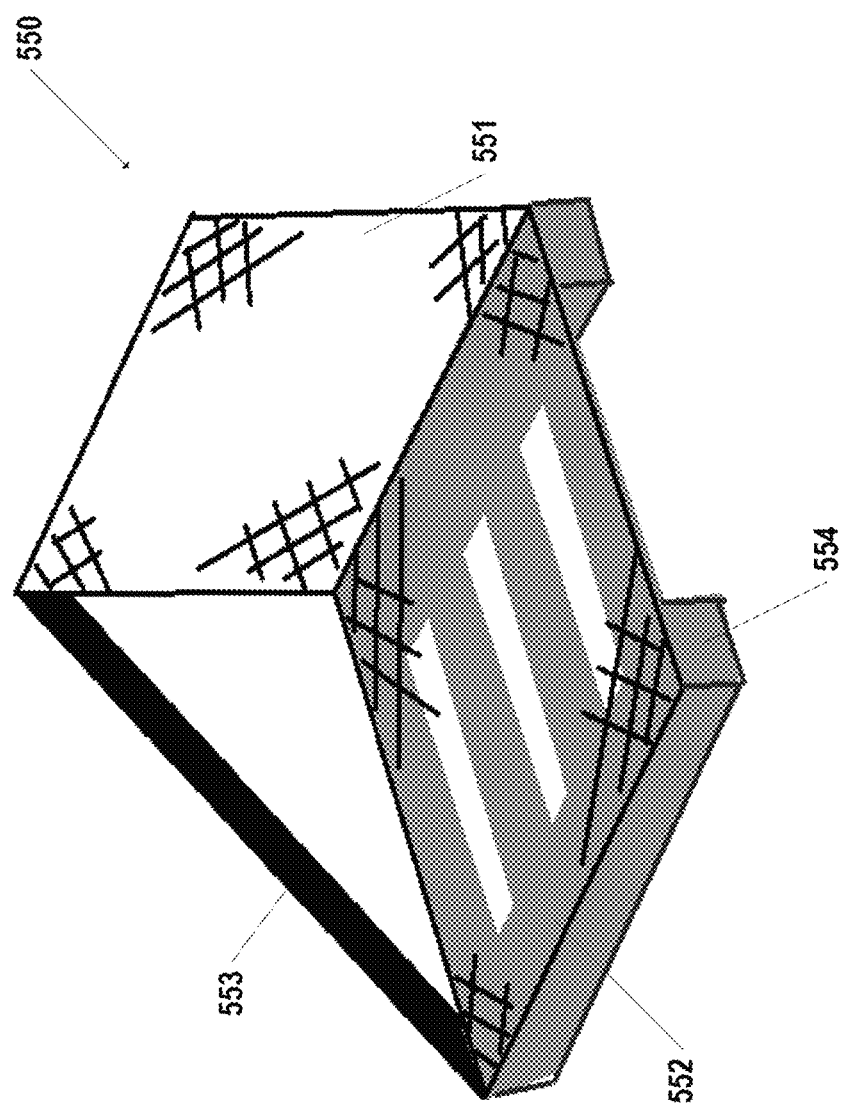
FIG. 4 illustrates another X-ray Penetration Grid according to various embodiments.

FIG. 4 illustrates a diagram of an XPG assembly 550 according to various embodiments. As shown in FIG. 4, the XPG assembly 550 may comprise a first grid portion 551, a second grid portion 552, and one or more supports 553. In various embodiments, the first grid portion 551 and second grid portion 552 may be in a perpendicular arrangement, and the support 553 may be configured to maintain the perpendicular arrangement. In various embodiments, a first end portion of the support 553 may be coupled to the first grid portion 551 using one or more fasteners such as those described above and a second end portion of the support may be coupled to the second grid portion 552 using one or more fasteners such as those described above. As a non-limiting example, the one or more fasteners may comprise a weld, an ultrasonic weld, an adhesive, a screw, a bolt, and/or the like. Moreover, as illustrated in FIG. 4, the XPG assembly 550 may be coupled to a support structure 554 or other transport vehicle. As non-limiting examples, such transport vehicles may comprise wooden pallets, plastic pallets, trailers, containers, crates, boxes, cages, luggage, cases, and/or the like. In various embodiments, the support structure 554 may be configured to facilitate movement of the XPG assembly 550 via a fork-truck without a separate pallet.

As previously mentioned, various embodiments described herein provide a unique XPG 150 that may be oriented relative to an X-ray scanning device 140 to ensure that the entire contents of a scanned item 10 have been penetrated. In addition to comprising radiopaque grid elements oriented so as to substantially prevent or minimize a ghosting phenomenon, the grid elements may provide a reference indicative of a unit of measure. For example, the grid elements may be spaced to form 1 inch square spaces there-between and may be utilized as a length reference for an item 10 being scanned.

The density of the material used within the mesh or grid structure is further sufficiently thick to absorb X-ray radiation penetrating the item(s) 10 being scanned (i.e., radiopaque), such that the mesh or grid structure appears in any resulting scanned image in an accurate and reliable manner only when the item(s) have been fully penetrated by the X-ray radiation 145 imposed thereon. In various embodiments, the material used within the mesh or grid structure is mild steel (plain-carbon steel), although any radiopaque material may be utilized. The mild steel used within the mesh or grid structure may have a density of approximately 7.85 g/cm$^3$, and may contain approximately 0.05% to 0.3% carbon measured by weight. The problem of shadowing or "ghosting" may be understood with reference to a non-limiting example of the screening of dense magazines and newspapers destined for passenger aircraft. Screening companies could not prove to the appropriate authority that they could see through the magazines and paperwork. Indeed, when examined with only partial grid or mesh structures placed adjacent packages, containers, and the like containing such dense items, X-ray imaging results indicated the existence of a full grid or mesh structure. In other words, as previously mentioned, the X-ray imaging results were shadowing or "ghosting" the remainder of the non-existing grid, thus rendering scan and/or penetration results ambiguous and inconclusive. Such ghost images may extend from the edges of one or more grid elements aligned at least substantially parallel to the direction of travel, and may appear superimposed over a dense item in the generated image.

From a practical perspective, the shadowing or "ghosting" should be understood to exist at least in part due to the relative orientation of the grid elements formed within such mesh or grid structures 150. For example, where such are aligned substantially parallel to the direction of travel of an item 10, a ghosted image may appear to include an extension of the mesh or grid structure such that a radiopaque object within the scanned item is obscured. A solution is to orient the grid elements within the grid or mesh structures other than at 0 or 90 degree angles relative to the direction of travel of the package. An optimal angle is at least substantially 45 degrees, although angles in ranges of +/−15 degrees relative to a 45 degree angle may be beneficial as well. Still other angular orientations may provide accurate results for particular applications. As previously noted, such angles relative to the direction of travel may be achieved utilizing an XPG having a first plurality of grid members 152 and second plurality of grid members 153 oriented such that angles α and β between the grid members and the frame 151 are at least substantially 45 degrees. Such XPG may be placed such that a first side of the frame is at least substantially parallel to the direction of travel.

The impact of ghosted images may be mitigated or substantially prevented when the XPG is oriented such that the first plurality of grid members 152 and second plurality of grid members 153 are neither parallel nor perpendicular to the direction of travel (e.g., at substantially 45 degrees to the direction of travel), such that the edges of the grid members 152, 153 are not substantially parallel to the direction of travel. As a non-limiting example, when the XPG is oriented such that the first plurality of grid members 152 and second plurality of grid members 153 are not parallel to the direction of travel (e.g., at substantially 45 degrees to the direction of travel), ghosted images of the grid or mesh structure are substantially, and in certain embodiments entirely, eliminated such that virtually no ghosted images are visible in the generated image. Moreover, in various circumstances, ghosting may be minimized or substantially prevented by orienting grid members 152, 153 such that they are neither parallel nor perpendicular to the direction of travel. Such orientation ensures no edges of grid elements 152, 153 are at least substantially parallel to the direction of travel, and therefore the resulting image does not comprise ghost images resembling extensions of one or more grid elements. By orienting the grid members 152, 153 such that they are neither parallel nor perpendicular to the direction of travel, any potential ghost images that may result from moving the item and XPG to the scanning location may be minimized or substantially prevented.

Orientation of an XPG Relative to an X-Ray Scanning Device

FIGS. 5A and 5B to FIGS. 9A and 9B illustrate schematic diagrams of exemplary methods of using an XPG according to various embodiments of the present invention.

Figure 5B:
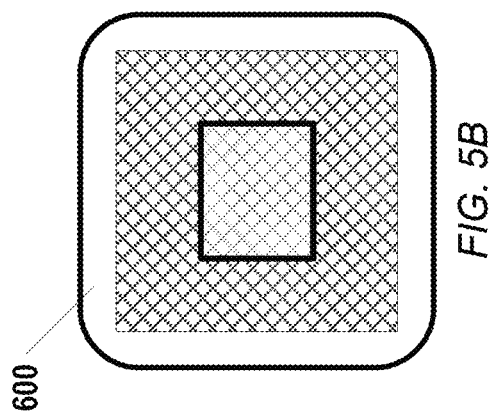
FIGS. 5A-5B are schematic diagrams of an X-ray Penetration Grid used with an X-ray scanner and a corresponding visual display according to various embodiments.
Figure 5A:
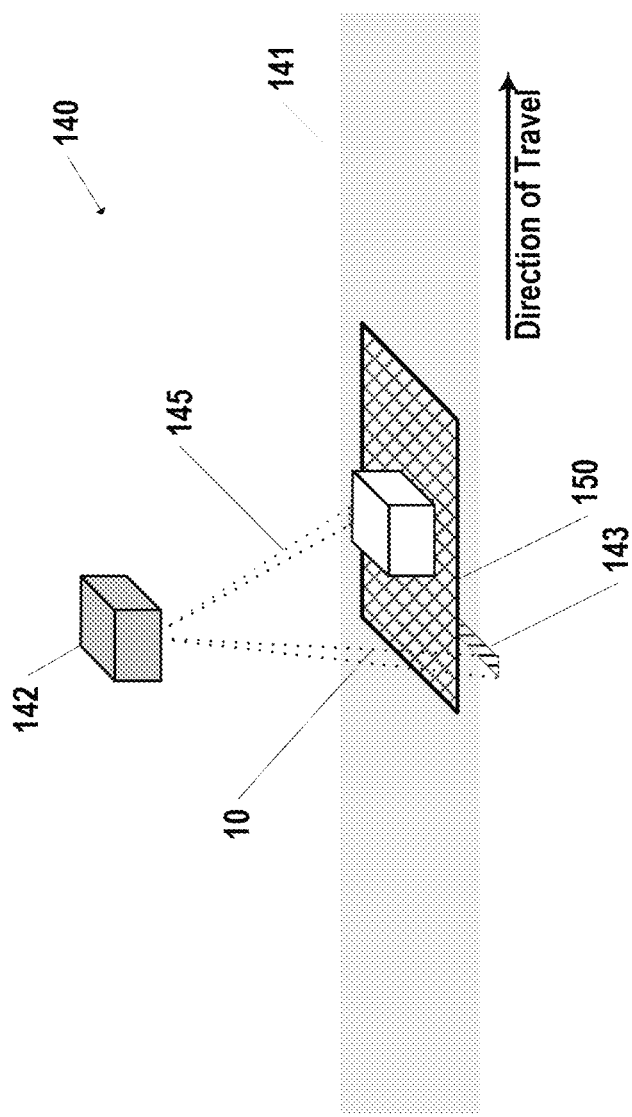

As shown in FIG. 5A, an XPG 150 may be utilized with an X-ray scanning device 140 utilizing an X-ray emitter 142 located above a conveying mechanism 141 according to various embodiments of the present invention. As illustrated in FIG. 5A, X-ray radiation (electromagnetic waves) 145 may be emitted from the X-ray emitter 142 and received by a detector 143. Although illustrated as a single component, the detector 143 may comprise a detector array comprising multiple detectors each comprising a conversion layer configured for receiving X-ray radiation and converting the received radiation into visible signals corresponding to the relative intensities of the received radiation. Thus, the X-ray scanning device 140 may be configured to scan one or more items 10 while the item is being propelled by the conveying mechanism 141. Although illustrated as a conveyor belt, the conveying mechanism may comprise any of a plurality of conveying mechanisms, such as, for example, a slide, chute, bottle conveyor, open or enclosed track conveyor, I-beam conveyor, cleated conveyor, and/or the like.

FIG. 5B illustrates an exemplary visual display 600 of the item 10 arranged on the XPG 150 being scanned. As illustrated therein, as least a portion of the grid or mesh structure located directly adjacent (e.g., above or below) the item 10 being scanned is still visible in the visual display 600. However, if a particularly dense object is contained within the item 10, the portion of grid or mesh structure located adjacent the dense object would not be visible in the visible display 600.

Referring again to FIG. 5A, in order to utilize the XPG 150, the XPG is oriented such that at least one side of the frame is parallel to the direction of travel of the conveying mechanism 141. Consequently, the first plurality of grid members 152 and second plurality of grid members 153 are oriented at an angle with respect to the direction of travel other than 90 degrees or 0 degrees (e.g., at least substantially 45 degrees). An item 10 to be scanned is placed such that the radiation 145 will pass through both the item and the XPG 150 before being received by the detector 143. As a non-limiting example, the item 10 may be placed on top of the XPG 150.

Figure 6B:
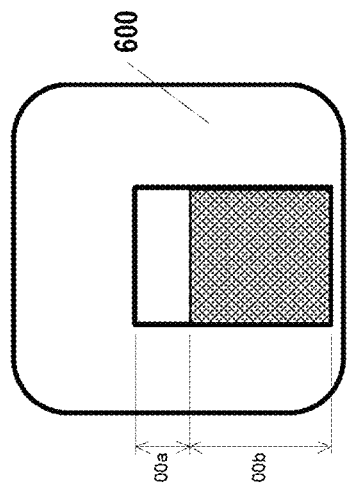
FIGS. 6A-6B are schematic diagrams of an X-ray Penetration Grid used with an X-ray scanner and a corresponding visual display according to various embodiments.
Figure 6A:
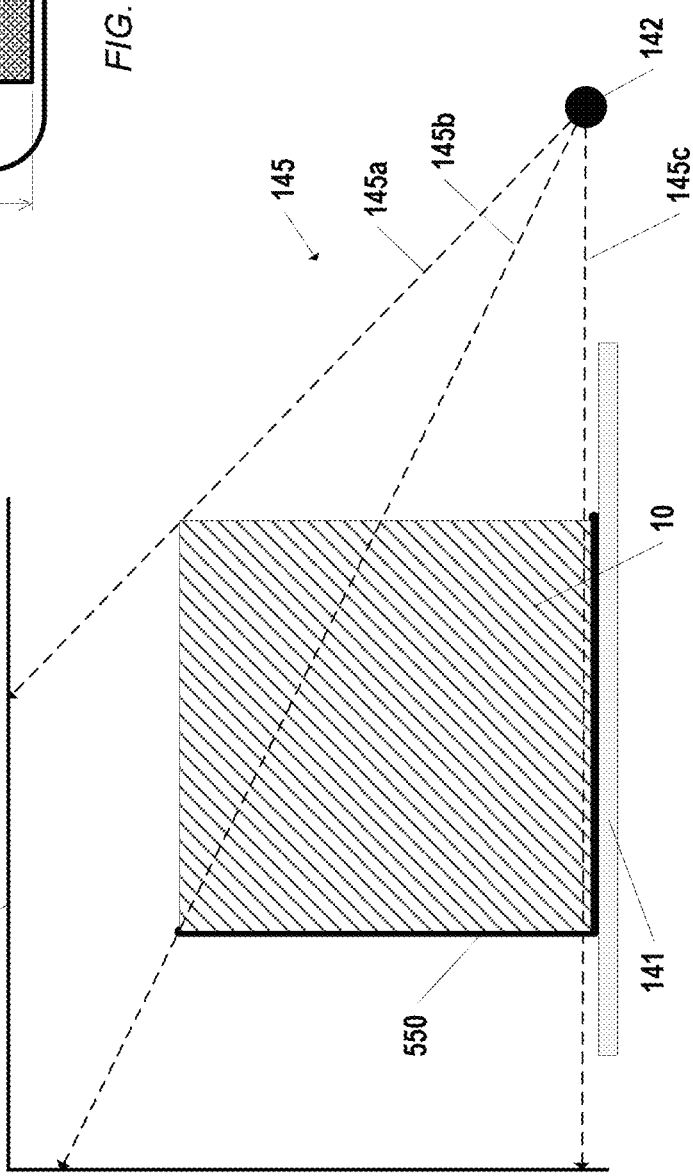

FIGS. 6A and 7A illustrate schematic diagrams of an item 10 being scanned by an X-ray scanning device 140 having an alternative configuration. Specifically, the X-ray emitter 142 shown in FIGS. 6A and 7A is located on a first side of the X-ray scanning device 140 and emits X-ray radiation 145 in a direction perpendicular to the direction of travel of the item 10. As shown in FIG. 6A, an XPG assembly 550 may be utilized such that at least one of the first grid portion 551 and second grid portion 552 is visible in the visible display 600. In various embodiments, each of the first grid portion 551 and second grid portion 552 may have a configuration substantially similar to XPG 150.

Referring now to FIG. 6A and the corresponding FIG. 6B, which illustrates an exemplary visual display 600 corresponding to a scanned item 10 having an orientation shown in FIG. 6A; at least a portion of the scanned item (located between radiation line 145a and radiation line 145b) is scanned without a corresponding portion of the XPG 550. Only the portion of the item 10 located between radiation line 145b and 145c (illustrated as portion 600b in FIG. 6B) is scanned with a corresponding portion of the XPG assembly 550 usable as a reference. Consequently, the XPG 550 does not provide a reference for determining whether an item was scanned throughout the entire depth of the item 10 over the portion of the item located between radiation line 145a and radiation line 145b (illustrated as portion 600a in FIG. 6B). Thus, a dense object located within this portion of the item 10 may not be identified by personnel operating the X-ray scanning device 140.

Referring now to FIG. 7A and the corresponding FIG. 7B, which illustrates an exemplary visual display 600 corresponding to a scanned item 10 having an orientation shown in FIG. 7A; the entirety of the item is scanned with a corresponding portion of the XPG assembly 550 usable as a reference. As illustrated in FIG. 7B, at least a portion of the XPG assembly 550 may be used as a reference for the entirety of the scanned item 10.

FIGS. 8A and 9A illustrate exemplary schematic diagrams of an item 10 being scanned by an X-ray scanning device 140 having yet another configuration. Specifically, the X-ray emitter 142 shown in FIGS. 8A and 9A is located above the item to be scanned 10 and on a first side of the item to be scanned.

Referring now to FIG. 8A and the corresponding FIG. 8B, which illustrates an exemplary visual display 600 corresponding to a scanned item 10 having an orientation shown in FIG. 8A; at least a portion of the scanned item (located between radiation line 145a and radiation line 145b) is scanned without a corresponding portion of the XPG assembly 550 usable as a reference, and at least a portion of the scanned item (located between radiation line 145c and 145d is scanned with two corresponding portions of the XPG such that the scanned area is obscured by the XPG. Only the portion of the item 10 between radiation line 145b and radiation line 145c (illustrated as portion 600b in FIG. 8A) is scanned with a single portion of the XPG assembly 550 usable as a reference. A dense object located in the portion of the item 10 between radiation line 145a and radiation line 145b (illustrated as portion 600a in FIG. 8B) may not be identified by personnel operating the X-ray scanning device 140. A dense object located in the portion of the item 10 between radiation line 145c and radiation line 145d (illustrated as portion 600c in FIG. 8B) may be obscured by the two portions of the XPG 550 through which the radiation passes between the X-ray emitter 142 and the detector 143.

Referring now to FIG. 9A and the corresponding FIG. 9B, which illustrates an exemplary visual display 600 corresponding to a scanned item 10 having an orientation shown in FIG. 9A; the entirety of the item is scanned with a single corresponding portion of the XPG assembly 550 usable as a reference. As illustrated in FIG. 9B, at least a portion of the XPG assembly 550 may be used as a reference for the entirety of the scanned item 10.

Method of Use

Figure 10A:
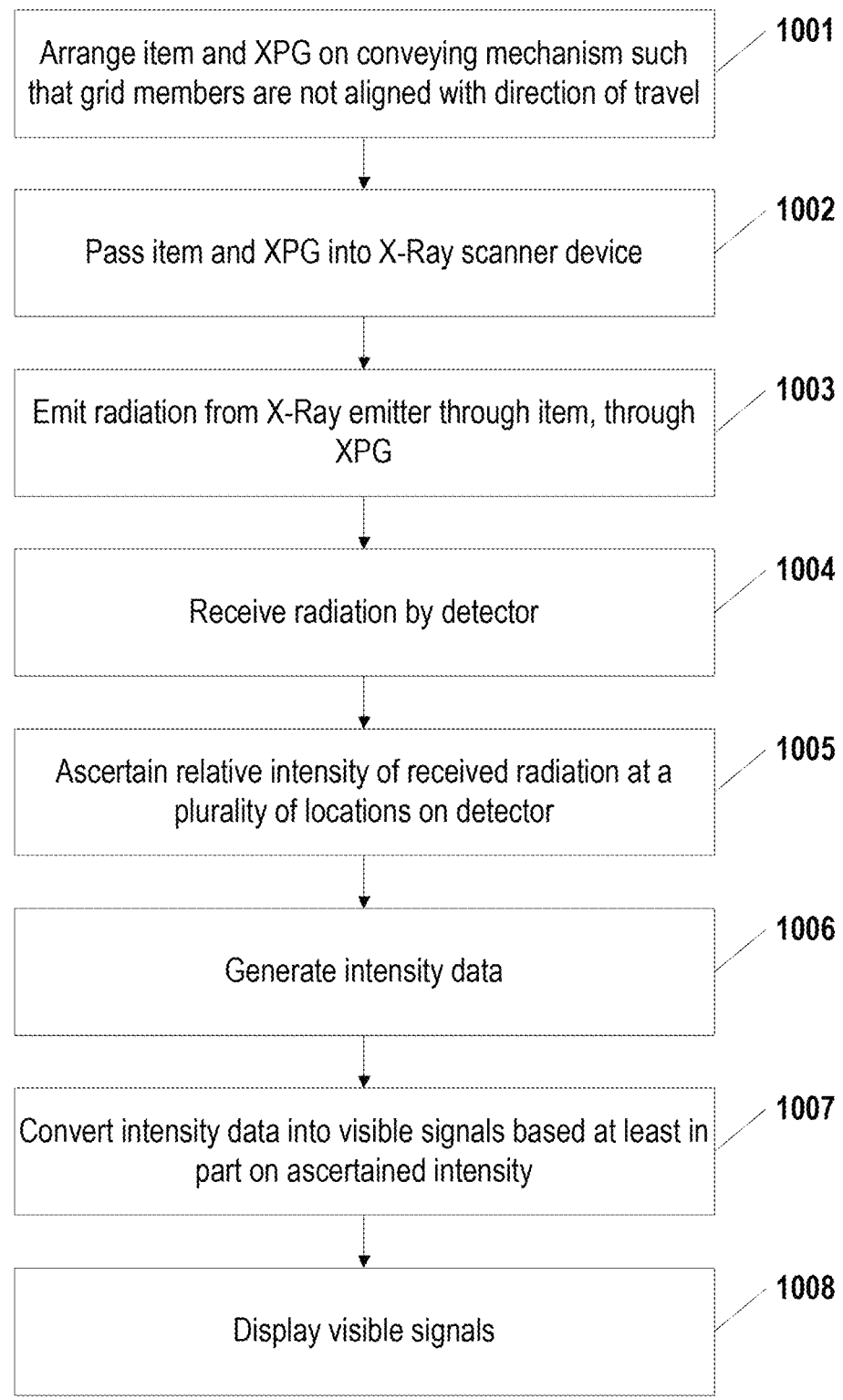
FIG. 10A illustrates a block diagram of a method of using an X-ray Penetration Grid according to various embodiments.

FIG. 10A illustrates an exemplary flowchart of a method of using an XPG 150 (or XPG assembly 550) according to various embodiments. As shown therein, the method begins at block 1001, wherein the item 10 and XPG 150 (or XPG assembly 550) is oriented relative to a conveying mechanism 141 such that the grid members 152, 153 are not parallel to the direction of travel of the conveying mechanism 141. As previously noted, the item 10 may be oriented relative the XPG 150 (or XPG assembly 550) such that radiation from the X-ray emitter 142 passes through both the item and XPG before reaching the detector. Preferably, the item 10 is arranged relative to the XPG 150 (or XPG assembly 550) such that radiation 145 cannot travel through any portion of the item without also passing through the XPG. Thus, the XPG 150 (or XPG assembly 550) may be used as a scan depth reference over the entirety of the scanned item 10.

Referring again to FIG. 10A, the item 10 and XPG 150 (or XPG assembly 550) is conveyed into the X-ray scanning device 140 at block 1002. The conveying mechanism 141 may be configured to propel an item 10 and XPG 150 (or XPG assembly 550) at a velocity such that the X-ray scanner device 140 may record multiple scans of each item while the item is within the X-ray scanner device. As a non-limiting example, the X-ray scanner device 140 may be configured to scan a plurality of slices of each item 10. Each successive slice may be at least substantially perpendicular to the direction of travel, and may be scanned as a portion of the item 10 is propelled through a scanning area. In various embodiments, the conveying mechanism 141 may operate continuously at a particular velocity, or it may be configured to temporarily stop moving while the X-ray scanner device 140 scans each item 10. While the item 10 and XPG 150 (or XPG assembly 550) are located within the X-ray scanning device 140, the X-ray emitter 142 emits X-ray radiation 145 through the item 10 and XPG 150 (or XPG assembly 550). In various embodiments, the X-ray emitter 142 may be operating constantly while the X-ray scanner device 140 is operating, such that the X-ray emitter 142 emits pulses of radiation to create X-ray images at least periodically (e.g., every 10 seconds, every 5 seconds, every second, every 500 milliseconds, every 250 milliseconds, every 100 milliseconds, every 10 milliseconds, and/or the like).

The radiation 145 emitted by the X-ray emitter 142 is received by the detector 143 at block 1004. At block 1005 the detector 143 determines the relative intensity of the radiation 145 received at each of a plurality of locations on the surface of the detector 143. The relative intensity of the radiation 145 received at each of the plurality of locations may be indicative of the location of various objects having differing densities within the item 10. The grid members 152, 153 of the XPG 150 (or XPG assembly 550) may be radiopaque, such that the detector 143 may detect a negligible or nonexistent intensity of radiation 145 at locations corresponding to the grid members. As a result, the relative intensity of the radiation 145 received by the detector 143 may be indicative of a radiopaque grid or mesh structure in addition to any radiation passed through the spaces in the grid or mesh structure of the XPG 150 (or XPG assembly 550).

At block 1006, the intensity data indicative of the relative intensity of the radiation 145 received by the detector 143 is generated. In various embodiments, the intensity data may be transmitted via one or more networks 130 to one or more central computing devices 110, the central server 200, one or more mobile devices 300, and/or one or more distributed computing devices 120.

As previously indicated, the detector 143 may trap a portion of the radiation 145 received from a previous emission 42 within the detector such that the radiation does not dissipate prior to receiving a subsequent emission of radiation. As a result, the intensity data generated based at least in part on the relative intensity of the radiation 145 received by the detector 143 may be amplified due to the trapped radiation present in the detector. As a simplified, non-limiting example, as a result of a first radiation emission by the X-ray emitter 142, the detector 143 determines that no items are placed on an XPG 150 (or XPG assembly 550). The intensity data generated by the detector 143 indicates that no radiation was received at locations corresponding to the radiopaque grid members 152, 153, and a maximum amount of radiation was received at all other locations (e.g., locations corresponding to the spaces between grid members). As a result of a second radiation emission by the X-ray emitter 142 occurring immediately following the first radiation emission (e.g., before the detector response generated based on the first emission fully decays), the detector 143 receives radiation with relative intensities indicative of a radiopaque object located on an XPG 150 (or XPG assembly 550). Therefore, at all locations corresponding to the radiopaque object, the detector receives substantially no radiation 145. However, because the previous detector response had not fully decayed, the generated intensity data corresponding to the second emission indicates that "ghost" radiation was received at all locations corresponding to the spaces between grid members 152, 153, including those detector locations also corresponding to the location of the radiopaque object. As a result, the intensity data may appear to indicate that the radiopaque object allowed a small amount of radiation 145 to pass there-through.

Although the previously presented example simplifies the process of receiving radiation 145 and generating intensity data including ghost radiation as the conveying mechanism 141 propels an item 10 and XPG 150 (or XPG assembly 550) into the X-ray scanning device 140, each of the plurality of locations of the detector 143 may receive varying intensities of radiation 145. Therefore, where an item 10 is oriented such that a volume of low density (allowing a higher intensity of radiation 145 to pass through the low density volume) is located downstream from a radiopaque volume, the ghosting phenomenon may impact the resulting intensity data corresponding to an emission passing through the radiopaque volume.

Figure 10B:
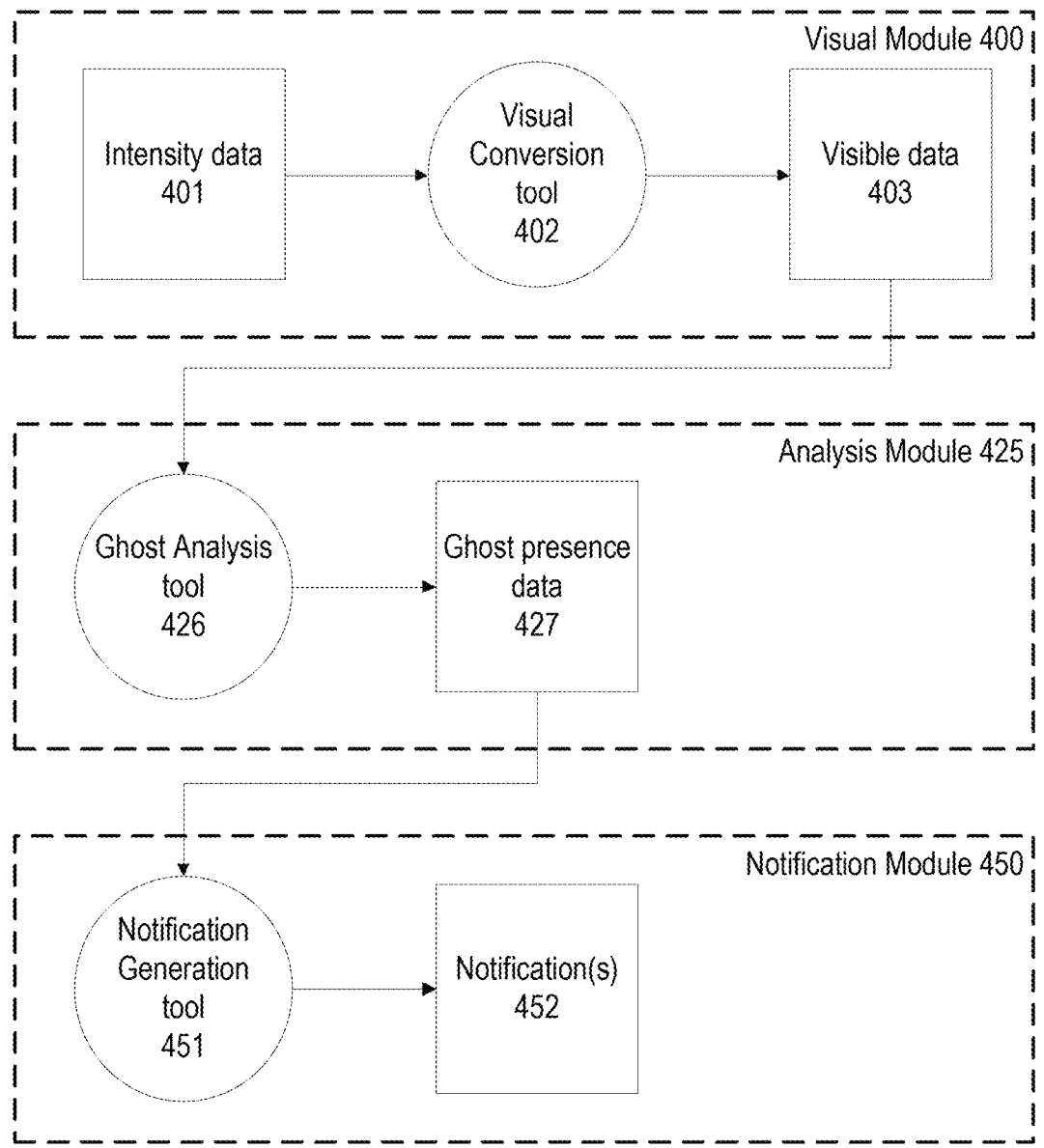
FIG. 10B is a schematic block diagram of a process flow as may be implemented via an visual module, an analysis module, and a notification module, as each are also illustrated in FIG. 2A according to various embodiments of the present invention.

FIG. 10B illustrates a schematic diagram of the various modules 400-450. In particular, FIG. 10B illustrates the relationship between the visual module 400, the analysis module 425, and the notification module 450. In various embodiments, the various modules 400-450 may facilitate implementation of various steps illustrated in FIG. 10A and described herein.

In various embodiments, the visual module 400 of the central server 200 may comprise a visual conversion tool 402 configured to convert the intensity data 401 received for each X-ray image into visible data 403 for each X-ray image comprising visible signals to be displayed via a display device at block 1007 of FIG. 10A. However, as will be understood by one skilled in the art, any of a variety of computing devices may be configured to convert the intensity data into visible signals. The resulting visible signals are displayed via a display device at block 1008.

As illustrated in FIG. 10B, the visual module 400 may transmit the visible data 403 to the analysis module 425 for additional processing. The analysis module 425 may be configured to identify the presence of ghost radiation signals in the visible data 403 for each X-ray image. As a non-limiting example, the analysis module 425 may comprise a ghost analysis tool 426 configured to generate ghost presence data 427 indicative of the presence of ghost signals in the X-ray image.

Because the grid members 152, 153 are not parallel to the direction of travel, no ghosted images may be present in the intensity data. However, where at least one grid member is oriented such that at least one edge of the radiopaque grid member is substantially parallel to the direction of travel, ghosted images may appear in the visible data 403. Therefore, the orientation of the grid members 152, 153 relative to the direction of travel may facilitate the identification of radiopaque objects within scanned items 10. As a non-limiting example, the analysis module 425 may be configured to identify radiopaque objects within an X-ray image based upon the presence of ghost grid lines appearing over a portion of the X-ray image. In various embodiments, upon a determination that ghost signals are present within the X-ray image, the analysis module 425 may be configured to transmit the ghost presence data to the notification module 450. The notification module 450 may comprise a notification generation tool 451 configured to generate and transmit one or more notifications 452 to relevant personnel indicative of the existence of ghost presence data 427 in an X-ray image. As a non-limiting example, the notification module 450 may be configured to illuminate an indicator light located proximate to a visual display configured to displaying the X-ray image data, or to display a notification message on the visual display. In response to receiving such notification, personnel monitoring the X-ray scanner device 140 may perform additional secondary screening on the item 10 in question. For example, such secondary screening may comprise reorienting the item 10 for an additional scan utilizing the X-ray scanner device 140, unpacking the item for a hand search of the contents of the item, and/or the like.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An X-ray detector system for determining the contents of an item, the system comprising:
    an X-ray emitter configured for emitting X-ray radiation;
    a detector comprising a receiving surface, the detector configured to receive the X-ray radiation and to generate one or more intensity signals indicative of an intensity of the received X-ray radiation at each of a plurality of locations on the receiving surface;

an X-ray penetration grid comprising a first grid structure comprising:

a perimeter surrounding the X-ray penetration grid having at least a first side, said first side being oriented in a first primary direction;

a first plurality of parallel grid members each having a first end and a second end; and a second plurality of parallel grid members each having a first end and a second end;

wherein:

the first end and the second end of each of the first plurality of parallel grid members intersects the perimeter at an angle such that the first plurality of parallel grid members are neither parallel nor perpendicular to the first side of the perimeter; and the first end and the second end of each of the second plurality of parallel grid members intersects the perimeter at an angle such that the second plurality of parallel grid members are neither parallel nor perpendicular to the first side of the perimeter; and a conveying mechanism configured for conveying the item and the X-ray penetration grid in a second primary direction to a location between the X-ray emitter and the detector, said second primary direction being substantially the same as the first primary of direction.

2. The X-ray detector system of claim 1, further comprising a user system comprising one or more memory and one or more processors, the user system configured to:

receive, via the one or more processors, the one or more intensity signals; and cause, via a display device, display of the intensity signals.

3. The X-ray detector system of claim 2, wherein the displayed intensity signals further comprise:

signals indicative of a current location of the item; and ghost signals indicative of ghosted images extending at least substantially parallel to said second primary direction.

4. The X-ray detector system of claim 3, further configured to generate, via the one or more processors, one or more notifications indicating the presence of ghost signals.

5. The X-ray detector system of claim 1, wherein each of the first plurality of parallel grid members is continuous and each of the second plurality of parallel grid members is continuous.

6. The X-ray detector system of claim 1, wherein the angle at which the first end of each of the first plurality of parallel grid members intersects the perimeter is between 30 degrees and 55 degrees.

7. The X-ray detector system of claim 6, wherein the angle at which the first end of each of the first plurality of parallel grid members intersects the perimeter is 45 degrees.

8. The X-ray detector system of claim 1, wherein each of the second plurality of parallel grid members is discontinuous.

9. The X-ray detector system of claim 1, wherein:

the first plurality of parallel grid members are spaced having at least substantially equivalent distances therebetween; and the second plurality of parallel grid members are spaced having at least substantially equivalent distances therebetween.

10. The X-ray detector system of claim 1, wherein the first plurality of parallel grid members and second plurality of parallel grid members are radiopaque.

11. The X-ray detector system of claim 1, wherein a portion of the X-ray radiation passes through the item, and the portion of the X-ray radiation that passes through the item also passes through the X-ray penetration grid.

12. The X-ray detector system of claim 1, wherein the x-ray penetration grid further comprises a second grid structure comprising:

a second perimeter surrounding the second grid structure having at least a first side;

a third plurality of parallel grid members each having a first end and a second end; and a fourth plurality of parallel grid members each having a first end and a second end, wherein:

the first end and the second end of each of the third plurality of parallel grid members intersects the second perimeter at an angle such that the third plurality of parallel grid members are neither parallel nor perpendicular to the first side of the second perimeter;

the first end and the second end of each of the fourth plurality of parallel grid members intersects the perimeter at an angle such that the fourth plurality of parallel grid members are neither parallel nor perpendicular to the first side of the second perimeter;

the first grid structure lies in a first plane; and the second grid structure lies in a second plane, the second plane being perpendicular to the first plane.

13. An X-ray detector system for determining the contents of an item, the system comprising:

an X-ray emitter configured for emitting X-ray radiation;

a detector comprising a receiving surface, the detector configured to receive the X-ray radiation and to generate one or more intensity signals indicative of an intensity of the received X-ray radiation at each of a plurality of locations on the receiving surface;

an X-ray penetration grid comprising a first grid structure comprising:

at least one side oriented in a first primary direction;

a first plurality of parallel grid members each having a first end and a second end; and a second plurality of parallel grid members each having a first end and a second end;

wherein:

the first end and the second end of at least a portion of the first plurality of parallel grid members intersect the at least one side at an angle such that the first plurality of parallel grid members are neither parallel nor perpendicular to the at least one side; and the first end and the second end of at least a portion of the second plurality of parallel grid members intersect the at least one side at an angle such that the second plurality of parallel grid members are neither parallel nor perpendicular to the at least one side; and a conveying mechanism configured for conveying the item and the X-ray penetration grid in a second primary direction to a location between the X-ray emitter and the detector, said second primary direction being substantially the same as the first primary of direction.

14. A computer implemented method for scanning an item, the method comprising steps for:

receiving, via a processor, one or more first intensity signals indicative of a first intensity of X-ray radiation received at each of a plurality of locations at a first scan time on a detector, wherein:
  the detector is configured to receive X-ray radiation from an X-ray emitter and to generate the one or more intensity signals indicative of an intensity of the received X-ray radiation at each of a plurality of locations on the receiving surface;
  the X-ray radiation is emitted from the X-ray emitter and at least a portion of the X-ray radiation passes through the item and an X-ray penetration grid before being received by the detector, wherein:
    the X-ray penetration grid comprises a first grid structure comprising:
      a perimeter surrounding the X-ray penetration grid having at least a first side, said first side being oriented in a first primary direction;
      a first plurality of parallel grid members each having a first end and a second end; and
      a second plurality of parallel grid members each having a first end and a second end;
      wherein:
        the first end and the second end of each of the first plurality of parallel grid members intersects the perimeter at an angle such that the first plurality of parallel grid members are neither parallel nor perpendicular to the first side of the perimeter; and
        the first end and the second end of each of the second plurality of parallel grid members intersects the perimeter at an angle such that the second plurality of parallel grid members are neither parallel nor perpendicular to the first side of the perimeter; and
    the item and the X-ray penetration grid are propelled in a second primary direction, said second primary direction being substantially the same as the first primary direction;
  causing, via a display device, display of the one or more first intensity signals;
  receiving, via the processor, one or more second intensity signals indicative of one or more ghosted images extending from an edge of the item;
  causing, via the display device, display of the one or more second intensity signals, wherein the displayed second intensity signals comprises a radiation ghost based at least in part on the one or more ghosted images; and
  identifying, via the one or more processors, the presence of a radiation ghost based at least in part on the second intensity signals.

15. The computer implemented method for scanning an item of claim 14, wherein a first portion of the X-ray radiation passes through the item, and the first portion of the X-ray radiation that passes through the item also passes through the X-ray penetration grid.

16. The computer implemented method for scanning an item of claim 14, further comprising steps for generating, via the one or more processors, a notification indicating the item requires additional processing to determine the item's contents.

17. The computer implemented method for scanning an item of claim 14, wherein the angle at which the first end of each of the first plurality of parallel grid members intersects the perimeter is between 30 degrees and 55 degrees.

18. The computer implemented method for scanning an item of claim 14, wherein the first plurality of parallel grid members and second plurality of parallel grid members are radiopaque.

19. The computer implemented method for scanning an item of claim 14, wherein a portion of the X-ray radiation passes through the item, and the portion of the X-ray radiation that passes through the item also passes through the X-ray penetration grid.

20. The computer implemented method for scanning an item of claim 14, wherein:
  the x-ray penetration grid further comprises:
    a second grid structure comprising:
      a second perimeter surrounding the second grid structure having at least a first side;
      a third plurality of parallel grid members each having a first end and a second end; and
      a fourth plurality of parallel grid members each having a first end and a second end;
      wherein:
        the first end and the second end of each of the third plurality of parallel grid members intersects the second perimeter at an angle such that the third plurality of parallel grid members are neither parallel nor perpendicular to the first side of the second perimeter;
        the first end and the second end of each of the fourth plurality of parallel grid members intersects the perimeter at an angle such that the fourth plurality of parallel grid members are neither parallel nor perpendicular to the first side of the second perimeter;
    the first grid structure lies in a first plane; and
    the second grid structure lies in a second plane, the second plane being perpendicular to the first plane; and
  a second portion of the X-ray radiation passes through the item and the second grid structure before being received by the detector such that the second portion of the X-ray radiation does not pass through the first grid structure.

* * * * *